(12) United States Patent
Hehrlein et al.

(10) Patent No.: US 8,142,412 B2
(45) Date of Patent: *Mar. 27, 2012

(54) METHOD AND APPARATUS FOR DELIVERING OXYGEN AND/OR OTHER GASES TO TISSUE

(75) Inventors: Christoph Hehrlein, Freiburg (DE); Michael Braun, Backnang (DE); John S. Geis, Bad Zwischenhahn (DE); Todd Davenport, Andover, MA (US)

(73) Assignee: Oxira Medical Inc., Boca Raton, FL (US)

(*) Notice: Subject to any disclaimer, the term of this patent is extended or adjusted under 35 U.S.C. 154(b) by 785 days.

This patent is subject to a terminal disclaimer.

(21) Appl. No.: 12/008,130

(22) Filed: Jan. 9, 2008

(65) Prior Publication Data

US 2008/0294086 A1 Nov. 27, 2008

Related U.S. Application Data

(63) Continuation-in-part of application No. 10/038,468, filed on Jan. 3, 2002, now Pat. No. 7,481,799.

(60) Provisional application No. 61/002,174, filed on Nov. 7, 2007.

(51) Int. Cl.
*A61M 31/00* (2006.01)
(52) U.S. Cl. .. 604/508; 604/21; 604/96.01; 604/103.02; 604/264; 604/509; 623/1.15
(58) Field of Classification Search .................. 604/500, 604/20–21, 23–24, 26, 93.01, 96.01, 103.02, 604/264, 506–510, 523; 600/585; 623/1.1, 623/1.15
See application file for complete search history.

(56) References Cited

U.S. PATENT DOCUMENTS

| | | | |
|---|---|---|---|
| 3,958,014 | A | 5/1976 | Watanabe et al. |
| 4,252,827 | A | 2/1981 | Yokoyama et al. |
| 4,366,169 | A | 12/1982 | White |
| 4,445,500 | A | 5/1984 | Osterholm |
| 4,636,195 | A | 1/1987 | Wolinsky |

(Continued)

FOREIGN PATENT DOCUMENTS

EP 0 112 658 A2 7/1984

(Continued)

OTHER PUBLICATIONS

Sass, D.J. et al., Gas Embolism Due to Intravenous FC 80 Liquid Fluorocarbon, Journal of Applied Physiology, 1976, pp. 745-751, vol. 40, Issue 5.

(Continued)

*Primary Examiner* — Theodore Stigell
(74) *Attorney, Agent, or Firm* — Pandiscio & Pandiscio

(57) ABSTRACT

A system comprising: a hollow tube having a distal end, a proximal end, and a lumen extending between the distal end and the proximal end; at least a portion of the tube comprising a porous membrane; and a gas-rich perfluorocarbon solution incorporated in the porous membrane; wherein the porous membrane has a porosity in the range of 0.001-200 microns, in order that: (i) the gas-rich perfluorocarbon solution is effectively incorporated into the porous membrane; and (ii) when the porous membrane is positioned in blood, the gas-rich perfluorocarbon solution elutes out of the porous membrane, in aggregations small enough to prevent the creation of embolisms in the blood, with the elution of the gas-rich perfluorocarbon solution into the blood varying between minutes and several hours, depending on the temperature and the hemodynamics of the blood.

56 Claims, 17 Drawing Sheets

U.S. PATENT DOCUMENTS

| | | | |
|---|---|---|---|
| 4,795,423 | A | 1/1989 | Osterholm |
| 4,909,252 | A | 3/1990 | Goldberger |
| 4,944,745 | A | 7/1990 | Sogard et al. |
| 5,023,052 | A | 6/1991 | Nagatomo et al. |
| 5,059,166 | A | 10/1991 | Fischell et al. |
| 5,084,011 | A | 1/1992 | Grady |
| 5,087,247 | A | 2/1992 | Horn et al. |
| 5,199,939 | A | 4/1993 | Dake et al. |
| 5,334,142 | A | 8/1994 | Paradis |
| 5,797,876 | A | 8/1998 | Spears et al. |
| 5,865,789 | A | 2/1999 | Hattler |
| 5,951,458 | A | 9/1999 | Hastings et al. |
| 5,976,119 | A | 11/1999 | Spears et al. |
| 6,048,332 | A | 4/2000 | Duffy et al. |
| 6,110,483 | A | 8/2000 | Whitbourne et al. |
| 6,146,358 | A | 11/2000 | Rowe |
| 6,235,007 | B1 | 5/2001 | Divino, Jr. et al. |
| 6,306,166 | B1 | 10/2001 | Barry et al. |
| 6,558,502 | B2 | 5/2003 | Divino, Jr. et al. |
| 7,481,799 | B2 * | 1/2009 | Hehrlein et al. ............ 604/264 |
| 2003/0066304 | A1 | 4/2003 | Becker et al. |
| 2003/0198798 | A1 | 10/2003 | Hehrlein et al. |

FOREIGN PATENT DOCUMENTS

| | | |
|---|---|---|
| EP | 0 372 088 A1 | 6/1990 |
| WO | WO 92/07594 | 5/1992 |
| WO | WO 97/32626 | 9/1997 |

OTHER PUBLICATIONS

Heinsen, H. et al., Pulmonary and Systemic Embolism After Deliberate Intravenous Fluorocarbon Administration, Virchows Archiv, Apr. 1980, pp. 331-341, vol. 386, No. 3.

Mattrey, Robert F. et al., Perfluorochemicals as US Contrast Agents for Tumor Imaging and Hepatosplenography: Preliminary Clinical Results, Radiology, May 1987, pp. 339-343, vol. 163.

Wall, TC et al., Intravenous Fluosol in the Treatment of Acute Myocardial Infarction, Circulation, 1994, pp. 114-120, vol. 90, American Heart Association.

Ferrari, Markus et al., Coronary Flow Analysis During Autoperfusion Angioplasty, Coronary Artery Disease, Nov./Dec. 1997, pp. 697-702, vol. 8, No. 11/12.

Tan, Walter A. et al., Long-Term Clinical Outcomes After Unprotected Left Main Trunk Percutaneous Revascularization in 279 Patients, Circulation, Oct. 2, 2001, pp. 1609-1614, vol. 104.

Kim, Hae Won et al., Artificial Oxygen Carriers as Red Blood Cell Substitutes: A Selected Review and Current Status, Artificial Organs, 2004, pp. 813-828, vol. 28, No. 9.

Hill, Steven E. et al., Cerebral Physiology of Cardiac Surgical Patients Treated With the Perfluorocarbon Emulsion, The Annals of Thoracic Surgery, Oct. 2005, pp. 1401-1407, vol. 80, Issue 4.

* cited by examiner

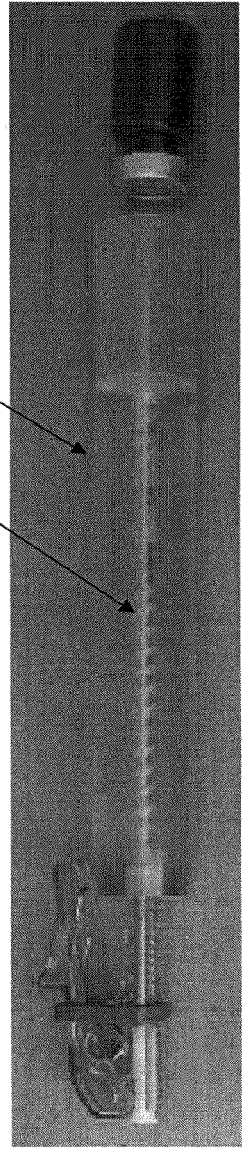
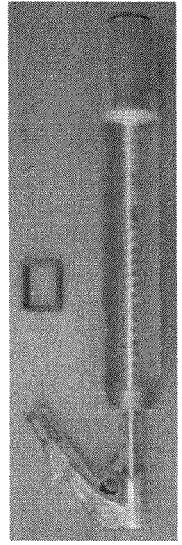
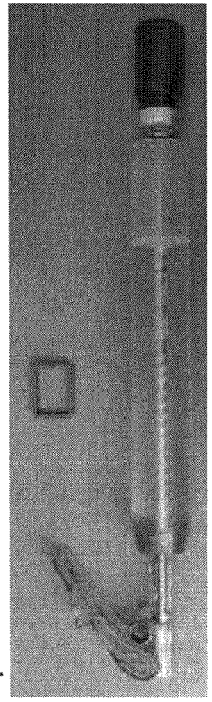
FIG. 4
FIG. 5

Step 3

Close the clip (which opens the hemostatic valve) and insert the balloon through the valve into the oxPFC vial until the catheter is completely immersed into the substance. Release the clip.

FIG. 6

Step 4

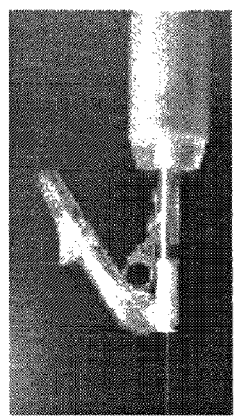

Leave the balloon in the OxPFC vial at a minimum of 1 minute for adequate loading of the oxygen. Close the clip (which opens the hemostatic valve) and remove the catheter out of the Activation Kit. Control the colour of the membrane, when it gets transparent, the loading time is sufficient. If membrane is not transparent, repeat step 3 to 4.

FIG. 7

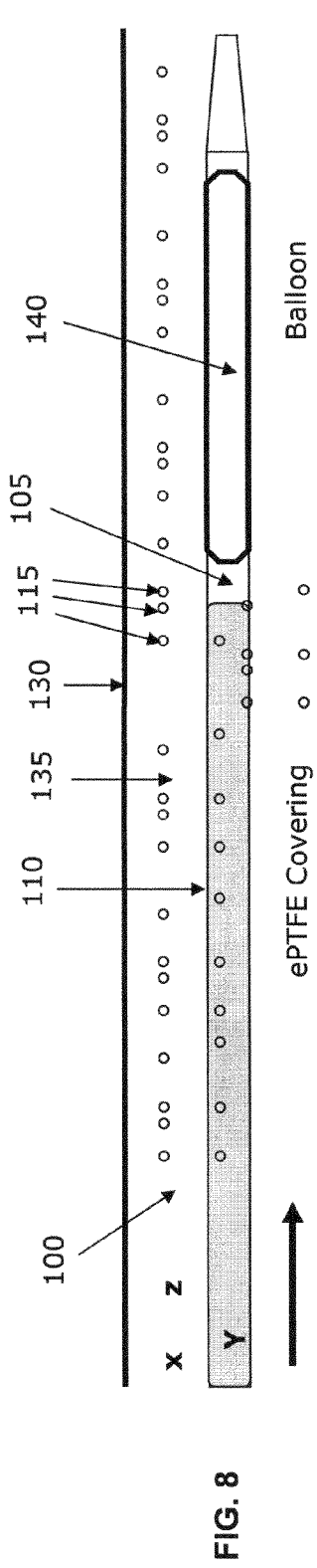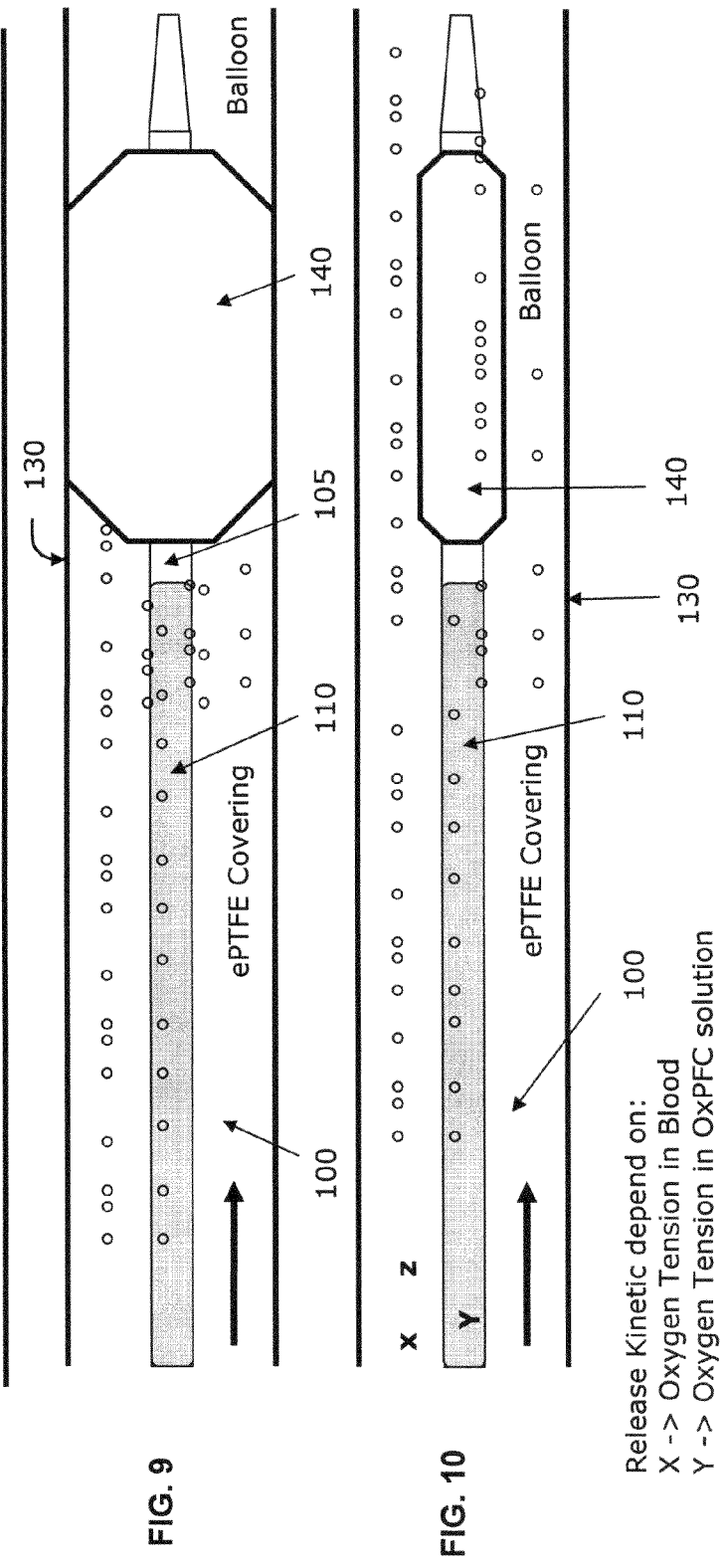
FIG. 8
FIG. 9
FIG. 10

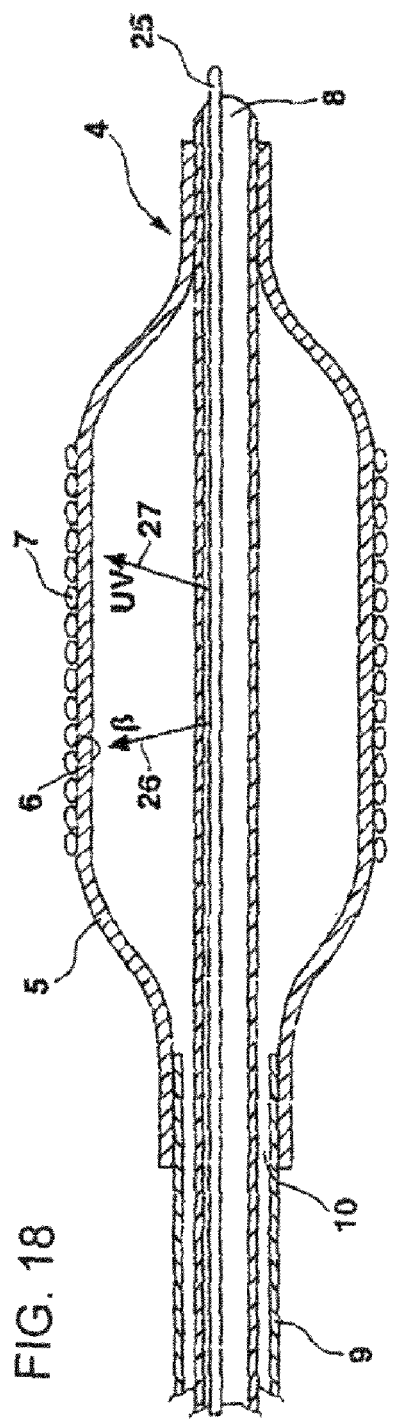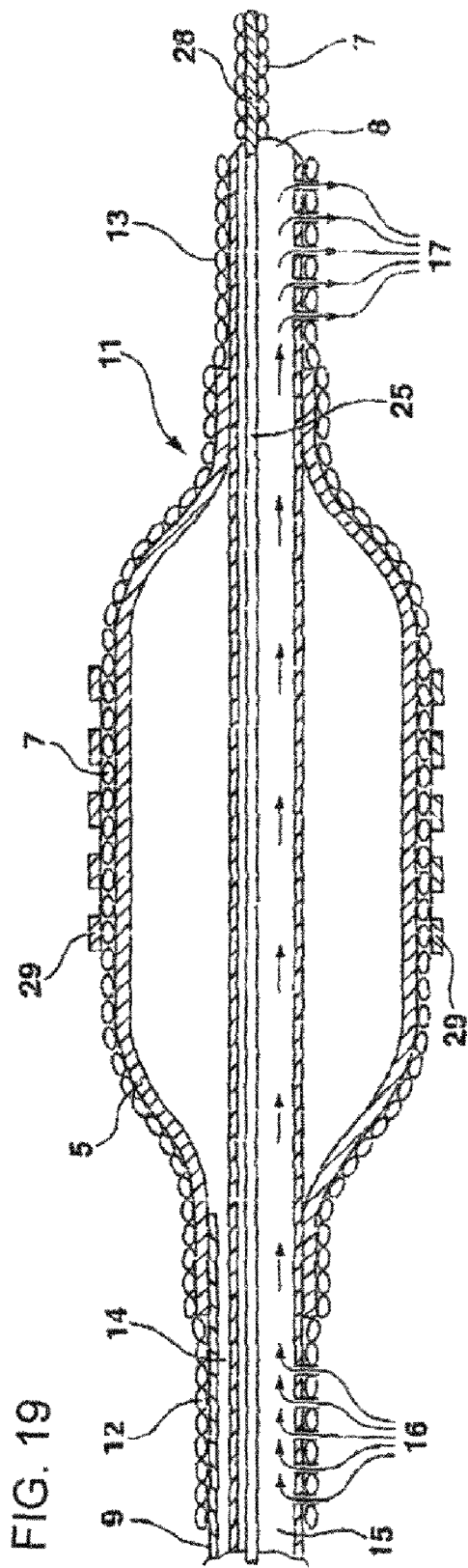

METHOD AND APPARATUS FOR DELIVERING OXYGEN AND/OR OTHER GASES TO TISSUE

REFERENCE TO PENDING PRIOR PATENT APPLICATIONS

This patent application:

(i) is a continuation-in-part of prior U.S. patent application Ser. No. 10/038,468, filed Jan. 3, 2002, now U.S. Pat. No. 7,481,799, by Christoph Hehrlein et al. for DELIVERY SOURCE OF OXYGEN; and (ii) claims benefit of prior U.S. Provisional Patent Application Ser. No. 61/002,174, filed Nov. 7, 2007 by Christoph Hehrlein et al. for METHOD AND APPARATUS FOR DELIVERING OXYGEN AND/OR OTHER GASES TO TISSUE.

The two above-identified patent applications are hereby incorporated herein by reference.

FIELD OF THE INVENTION

This invention relates to percutaneously delivering oxygen and/or other gases to tissue for the treatment of cardiovascular disease and/or for other treatment purposes. Among other things, the method and apparatus disclosed herein may be used to reduce the risks of ischemic events during an angioplasty procedure and/or a plaque removal procedure, to improve healing of hypoxic tissues, and/or to slow down restenosis after vascular interventions.

BACKGROUND OF THE INVENTION

A percutaneous transluminal angioplasty (PTA) of blood vessels, including the coronary arteries (PTCA), is a very common procedure to reduce vessel narrowing (i.e., stenosis) that obstructs blood flow to tissue, especially human organs. The angioplasty procedure typically involves inflating a balloon within the constricted region of the blood vessel so as to re-open the blood vessel. The success rates of coronary angioplasty procedures are typically inversely related to (i) the extent of the vascular disease, and (ii) the patient's intolerance to myocardial ischemia (i.e., blood flow obstruction) during the temporary blood vessel occlusion which is associated with a PTA procedure.

More particularly, one of the principle limitations of a coronary angioplasty procedure is the complete obstruction of blood flow during the inflation of the angioplasty balloon. After a short period of balloon occlusion, patients experience myocardial ischemia due to the interruption of oxygenated blood to the myocardium. Myocardial ischemia is usually indicated by angina pectoris and/or cardiac arrhythmias.

In the past, several perfusion balloon catheters have been developed to overcome the problem of total blood flow obstruction during percutaneous coronary interventions. By way of example but not limitation, U.S. Pat. No. 4,944,745 (Sograd) discloses a perfusion balloon catheter that allows passive perfusion of blood through a catheter whose balloon is obstructing blood flow. U.S. Pat. No. 4,909,252 (Goldberger) discloses a perfusion balloon catheter with a central opening which allows blood flow through the catheter when the balloon is fully inflated. U.S. Pat. No. 5,087,247 (Horn et al.) discloses a balloon perfusion catheter with an elongated flexible perfusion shaft, with multiple openings proximal and distal to the balloon, in order to permit blood flow through an artery during balloon inflation. International Patent Publication No. WO 9732626 (Cox et al.) discloses an inflatable balloon envelope allowing blood passage during inflation of the device.

While such perfusion balloon catheters permit some continued blood flow while their balloons are inflated, they are nonetheless limited to a flow rate which is something less than the normal flow rate of the blood passing through the vessel. In other words, perfusion balloon catheters can provide, at best, only some fraction of the normal flow rate which existed in the blood vessel prior to insertion of the catheter and inflation of the balloon. Thus, when perfusion balloon catheters are placed into relatively small arteries (e.g., the coronary arteries) which already have modest flow rates, the further reduction of an already-low flow rate is frequently clinically unacceptable. The inadequacies of the perfusion balloon catheter were characterized in a publication by Ferrari et al. (Coronary Artery Disease, 1997) who conclude their studies with the statement that in "high-risk patients dependent on adequate coronary perfusion, autoperfusion balloons are not able to provide sufficient distal coronary blood flow during balloon inflation".

Insufficient blood flow distal to an inflated balloon causes ischemia and hence hypoxia (i.e., oxygen deprivation) in tissue (e.g., the end organs) because the oxygenation of tissue previously supplied with blood is reduced.

For this reason, angioplasty in the coronary arteries is a relatively high risk procedure in patients who require dilatation of the unprotected trunk of the left main coronary artery. Tan et al. (Circulation, 2001) concluded that although percutaneous balloon interventions are a generally accepted treatment modality for coronary artery disease, left main PTCA procedures remain a high risk procedure for the patient.

Another limitation of a coronary angioplasty is restenosis. Restenosis after a PTCA procedure has been successfully inhibited by ionizing radiation therapy (i.e., brachytherapy) applied prior to, or shortly after, angioplasty. Thus, vascular brachytherapy using radioactive sources has become a new treatment option to prevent restenosis. More particularly, radioactive stents disclosed in U.S. Pat. No. 5,059,166 (Fischell et al.) and/or radioactive catheters disclosed in U.S. Pat. No. 5,199,939 (Dake et al.) have been used to minimize or eliminate neointimal hyperplasia after angioplasty. However, the logistical complexities of using radiation sources in coronary arteries, and radiation safety issues, have prompted researchers to improve the irradiation technology. To this end, U.S. Pat. No. 5,951,458 (Hastings et al.) discloses a radiation catheter that releases oxidizing agents such as $H_2O_2$ to prevent restenosis after a cardiovascular intervention. The method described by Hastings et al. helps to reduce the radiation doses, or treatment times, necessary to prevent restenosis.

Oxygenated perfluorocarbon (PFC) emulsions have been used to treat ischemic and hypoxic disorders. Oxygen-transferable PFC emulsions became known as artificial blood substitutes more than twenty years ago. By way of example but not limitation, in U.S. Pat. No. 3,958,014 (Watanabe et al.) and U.S. Pat. No. 4,252,827 (Yokoyama et al.), perfluorocarbon (PFC) emulsions are disclosed that have a small PFC "particle" size of 0.02 microns to 0.25 microns, and which were injected into the bloodstream. Additionally, U.S. Pat. No. 4,445,500 (Osterholm) teaches that oxygenated perfluorocarbon (PFC) emulsions can be injected into the cerebrospinal pathway to improve aerobic respiration of tissue. Furthermore, U.S. Pat. No. 4,795,423 (Osterholm) discloses an intraocular perfusion with perfluorinated substances to treat ischemic retinopathy.

Unfortunately, clinical experience has shown that the current approaches for using PFCs to oxygenate tissue are highly problematic. More particularly, and as will hereinafter be discussed in further detail, the current approaches for using perfluorocarbons (PFCs) prevent the use of "pure" PFC solutions and, instead, require the use of PFC emulsions. These emulsions themselves introduce a whole new set of problems which effectively limit the clinical use of PFCs in the bloodstream.

More particularly, it has been found that a pure perfluorocarbon (PFC) solution, with or without a "passenger" gas (e.g., oxygen), cannot be safely injected directly into the arterial or venous bloodstream, e.g., using a standard intravenous (IV) line or syringe. This is because introducing pure PFC solutions in this manner creates dangerous (and potentially fatal) embolisms in the bloodstream. These embolisms are created due to the fact that the PFCs are hydrophobic and are not soluble in blood. Thus, when a pure PFC solution is injected directly into the bloodstream (e.g., for hyperoxic medical therapy), the PFC tends to aggregate into relatively large bodies (or "particles") within the bloodstream. These relatively large aggregations of PFC tend to create embolisms in the bloodstream. For this reason, introducing pure PFCs (with or without a "passenger" gas) directly into the bloodstream, without the provision of some sort of PFC-dispersing mechanism, is not feasible due to the creation of dangerous embolisms.

Furthermore, it is not possible to eliminate the problematic PFC aggregations by simply diluting the PFC with another liquid prior to its introduction into the bloodstream, because the PFCs are not easily soluble in biocompatible fluids (e.g., the PFCs are insoluble in saline). Thus, the PFC tends to re-aggregate even when it is diluted with another liquid, so that the problematic PFC aggregations remain.

As a result, and as noted above, emulsifying agents (such as egg yolk, phospholipids, Pluronic-F68 and other emulsifiers) have been added to the PFC prior to the injection of the PFC into the bloodstream, whereby to "break up" the PFC particles and minimize aggregations of the PFC within the bloodstream. See, for example, U.S. Pat. Nos. 3,958,014 (Watanabe et al.), 4,252,827 (Yokoyama et al.), 4,445,500 (Osterholm) and 4,795,423 (Osterholm). Thus, with the prior art approach, emulsifying agents are used as a PFC-dispersing mechanism to break up the PFC and prevent the problematic PFC aggregations which can lead to embolisms.

However, clinical studies in humans evaluating such PFC emulsions (e.g., Fluosol and others) have shown that the use of these emulsions, infused into blood with the PFC for hyperoxic therapy, can cause respiratory insufficiency and pulmonary edema (Wall T C et al., Circulation 1994), most likely due to fluid overload and subsequent congestive heart failure. Thus, PFC emulsions can be considered as PFC "particles" (i.e., aggregations) that are accompanied by large quantities of another therapeutic agent (i.e., the emulsifier) which serves to emulsify (i.e., disperse) the pure PFC within the bloodstream. However, these large quantities of additional therapeutic agent (i.e., the emulsifier) in turn significantly increase intravascular volumes and thereby induce unwanted side effects such as respiratory insufficiency and pulmonary edema.

In addition, PFC emulsions are capable of uploading and releasing, per unit of volume, far less oxygen than a pure PFC solution. Thus, where emulsions are added to the PFC in order to avoid the creation of embolisms, it is generally necessary to provide additional systemic oxygenation to the patient via the lung (e.g., by breathing 100% oxygen) so as to create a sufficiently therapeutic oxygen tension of the PFC emulsions (Kim H W et al., Artificial Organs, Vol. 28, No. 9 2004). However, such intensive systemic oxygenation is normally to be avoided clinically, due to the adverse affects of elevated oxygen concentration on the lungs (e.g., oxygen toxicity) (Kim H W et al., Artificial Organs, Vol. 28, No. 9 2004).

Moreover, the use of emulsions to disperse the PFC in blood can also cause allergic reactions in the patient. Mattrey et al. showed that PFC emulsions can cause allergic reactions (Mattrey R F et al., Radiology 1987). More particularly, in an investigation of Fluosol-DA 20% as a contrast agent using Pluronic-F68 and others as emulsifiers for PFC in humans, it was reported that Fluosol-DA 20% caused allergic reactions which are most likely triggered by complement activation of the substance Pluronic-F68 (Mattrey R F et al., Radiology 1987). Since pure PFCs are chemically inert and contain no emulsifiers, no allergic reactions are to be expected when using pure PFCs in the blood; thus it has been concluded that it is the presence the emulsifiers which trigger the allergic reaction in the patient.

For these reasons, using oxygenated PFCs in conjunction with emulsifiers to prevent hypoxia has not heretofore been clinically successful.

Thus it will be seen that pure PFCs (with or without a "passenger" gas) cannot be introduced directly into the bloodstream without also providing some PFC-dispersing mechanism to prevent embolisms. However, it will also be seen that the prior art approach of using emulsions as the PFC-dispersing mechanism for the PFC introduces a whole new set of problems which effectively limit the clinical use of PFCs in the bloodstream.

For these reasons, prior art PFC systems for delivering oxygen to tissue have not heretofore been clinically successful.

SUMMARY OF THE INVENTION

The present invention provides a radically new (i.e., non-emulsifier) PFC-dispersing mechanism to permit the introduction of a pure PFC solution in the bloodstream while preventing the formation of large, embolism-inducing PFC aggregations in the bloodstream.

More particularly, the present invention employs a carefully constructed porous membrane (which may also be referred to as a porous substrate) to safely dispense pure, chemically inert PFCs directly into the bloodstream at sufficiently low rates, and in sufficiently small bodies, as to prevent the creation of the aforementioned large PFC aggregations which lead to embolisms.

This carefully constructed porous membrane may be mounted on, and/or disposed within and/or otherwise carried by, a catheter or wire or other intravascular device or structure (e.g., an atherectomy device, a stent, etc.); a pure PFC solution loaded into the porous membrane; and the catheter or wire or other intravascular device or structure advanced into the vascular system of the patient so that the porous membrane is located at a selected site within the bloodstream; whereupon the porous membrane will act as a PFC-dispersing mechanism to dispense the pure PFC solution directly into the bloodstream—in a carefully controlled, highly dispersed manner—so that micro-, nano-, and subnano-sized quantities of PFC molecules safely enter the bloodstream, without the occurrence of large, embolism-inducing PFC aggregations. The pure PFC solution preferably carries a sizable quantity of therapeutic gas (e.g., oxygen) therein, so that the gas-rich (e.g., oxygen-rich) PFC solution can deliver the therapeutic gas to downstream tissue (e.g., for oxygenation purposes).

An important aspect of the present invention is that the porous membrane must be carefully constructed so as to permit the gas-rich (e.g., oxygen-rich) PFC to enter the bloodstream at the appropriate rate. In fact, it has been discovered that it is important to form the porous membrane with a porosity which permits the gas-rich PFC to disperse into the bloodstream in very small volumes, and at a highly controlled rate which is both (i) sufficiently high to provide therapeutic benefit to the patient by the delivery of adequate quantities of therapeutic gas (e.g., oxygen) molecules to tissue, and (ii) sufficiently low so as to avoid the creation of embolisms in the bloodstream, even when using pure PFC solutions.

In practice, it has been discovered that, for a catheter or wire or other intravascular device or structure (e.g., atherectomy device, stent, etc.) placed into an artery having a typical rate of blood flow, forming the porous membrane with a porosity in the range of 0.001-200 microns, and preferably in the range of 20-200 microns, permits appropriate dispersion of the gas-rich PFC into the bloodstream without inducing embolisms.

It has been discovered that a pore size of greater than 200 microns can increase the likelihood of creating embolisms in the bloodstream.

It has also been discovered that a pore size which is too small (e.g., less than 20 microns) can make it difficult to deliver enough gas molecules to a site to provide certain therapeutic benefits. Thus, for example, where it is desired to provide oxygenation therapy in larger diameter blood vessels, it may not be desirable to use a pore size of less than 20 microns, since this may not provide enough oxygen molecules to the downstream tissue. However, where the oxygenation therapy is to be provided in smaller diameter vessels, or where some other, non-oxygenation therapy is to be provided to the patient, smaller quantities of therapeutic gas molecules may be adequate, in which case smaller pore sizes (e.g., 0.001 microns) may be satisfactory.

It has been discovered that, for oxygenation therapy, a pore size of 20-200 microns provides excellent therapeutic benefits while still preventing the creation of embolisms.

In one preferred form of the invention, there is provided a system comprising:
a hollow tube having a distal end, a proximal end, and a lumen extending between the distal end and the proximal end;
at least a portion of the tube comprising a porous membrane; and
a gas-rich perfluorocarbon solution incorporated in the porous membrane;
wherein the porous membrane has a porosity in the range of 0.001-200 microns, in order that:
(i) the gas-rich perfluorocarbon solution is effectively incorporated into the porous membrane; and
(ii) when the porous membrane is positioned in blood, the gas-rich perfluorocarbon solution elutes out of the porous membrane, in aggregations small enough to prevent the creation of embolisms in the blood, with the elution of the gas-rich fluorocarbon solution into the blood varying between minutes and several hours, depending on the temperature and the hemodynamics of the blood.

In another form of the invention, there is provided a system comprising:
a medical wire;
at least a portion of the medical wire comprising a porous membrane; and
a gas-rich perfluorocarbon solution incorporated in the porous membrane;
wherein the porous membrane has a porosity in the range of 0.001-200 microns, in order that:
(i) the gas-rich perfluorocarbon solution is effectively incorporated into the porous membrane; and
(ii) when the porous membrane is positioned in blood, the gas-rich perfluorocarbon solution elutes out of the porous membrane, in aggregations small enough to prevent the creation of embolisms in the blood, with the elution of the gas-rich fluorocarbon solution into the blood varying between minutes and several hours, depending on the temperature and the hemodynamics of the blood.

In another form of the invention, there is provided a method for treating a patient, comprising:
providing:
(i) a hollow tube having a distal end, a proximal end, and a lumen extending between the distal end and the proximal end, at least a portion of the tube comprising a porous membrane; and
(ii) a gas-rich perfluorocarbon solution;
loading the gas-rich perfluorocarbon solution into the porous membrane; and
positioning the tube in the vascular system of the patient so that porous membrane is exposed to blood;
wherein the porous membrane has a porosity in the range of 0.001-200 microns, in order that:
(i) the gas-rich perfluorocarbon solution is effectively incorporated into the porous membrane; and
(ii) when the porous membrane is positioned in blood, the gas-rich perfluorocarbon solution elutes out of the porous membrane, in aggregations small enough to prevent the creation of embolisms in the blood, with the elution of the gas-rich perfluorocarbon solution into the blood varying between minutes and several hours, depending on the temperature and the hemodynamics of the blood.

In another form of the invention, there is provided a method for treating a patient, comprising:
providing:
(i) a medical wire, at least a portion of the medical wire comprising a porous membrane; and
(ii) a gas-rich perfluorocarbon solution;
loading the gas-rich perfluorocarbon solution into the porous membrane; and
positioning the medical wire in the vascular system of the patient so that porous membrane is exposed to blood;
wherein the porous membrane has a porosity in the range of 0.001-200 microns, in order that:
(i) the gas-rich perfluorocarbon solution is effectively incorporated into the porous membrane; and
(ii) when the porous membrane is positioned in blood, the gas-rich perfluorocarbon solution elutes out of the porous membrane, in aggregations small enough to prevent the creation of embolisms in the blood, with the elution of the gas-rich perfluorocarbon solution into the blood varying between minutes and several hours, depending on the temperature and the hemodynamics of the blood.

In another form of the invention, there is provided an intravascular treatment device comprising:
an intravascular device having a distal end and a proximal end;
at least a portion of the intravascular device comprising a porous membrane; and
a perfluorocarbon solution incorporated in the porous membrane;

wherein the porous membrane has a porosity in the range of 0.001-200 microns, in order that:
  (i) the perfluorocarbon solution is effectively incorporated into the porous membrane; and
  (ii) when the porous membrane is positioned in blood, the perfluorocarbon solution elutes out of the porous membrane, in aggregations small enough to prevent the creation of embolisms in the blood.

In another form of the invention, there is provided a method for treating a patient, comprising:
  providing:
    an intravascular device having a distal end and a proximal end;
    at least a portion of the intravascular device comprising a porous membrane; and
    a perfluorocarbon solution;
  loading the perfluorocarbon solution into the porous membrane; and
  positioning the intravascular device in the vascular system of the patient so that porous membrane is exposed to blood;
  wherein the porous membrane has a porosity in the range of 0.001-200 microns, in order that:
    (i) the perfluorocarbon solution is effectively incorporated into the porous membrane; and
    (ii) when the porous membrane is positioned in blood, the perfluorocarbon solution elutes out of the porous membrane, in aggregations small enough to prevent the creation of embolisms in the blood.

In another form of the invention, there is provided an intravascular treatment device comprising:
  an intravascular device having a distal end and a proximal end; and
  at least a portion of the intravascular device comprising a porous membrane;
  wherein the porous membrane has a porosity in the range of 0.001-200 microns, in order that when a perfluorocarbon solution is introduced to the porous membrane:
    (i) the perfluorocarbon solution is effectively incorporated into the porous membrane; and
    (ii) when the porous membrane is positioned in blood, the perfluorocarbon solution elutes out of the porous membrane, in aggregations small enough to prevent the creation of embolisms in the blood.

BRIEF DESCRIPTION OF THE DRAWINGS

These and other objects, features and advantages of the present invention will be more fully disclosed in, or rendered obvious by, the following detailed description of the preferred embodiments of the invention, which is to be considered together with the accompanying drawings wherein like numbers refer to like parts, and further wherein:

FIGS. 4-7 are schematic views showing how the catheter's porous membrane may be loaded with gas-rich (e.g., oxygen-rich) PFC;

FIGS. 8-10 are schematic views illustrating how a balloon catheter, incorporating the porous membrane and the gas-rich PFC of the present invention, may be deployed in a blood vessel, so that the gas-rich PFC elutes out of the porous membrane and into the bloodstream;

FIG. 18 is a schematic longitudinal view of a novel balloon catheter formed in accordance with the present invention, with the balloon carrying the porous membrane and with the porous membrane carrying the gas-rich (e.g., oxygen-rich) PFC in accordance with the present invention;

FIG. 19 is a schematic longitudinal view of a stent delivery system comprising a porous membrane for appropriately dispersing a supply of gas-rich (e.g., oxygen-rich) PFC—in this embodiment, the porous membrane is located on the shaft of the catheter, proximally and/or distally to the balloon;

DETAILED DESCRIPTION OF THE PREFERRED EMBODIMENTS

In General

Figure 1:
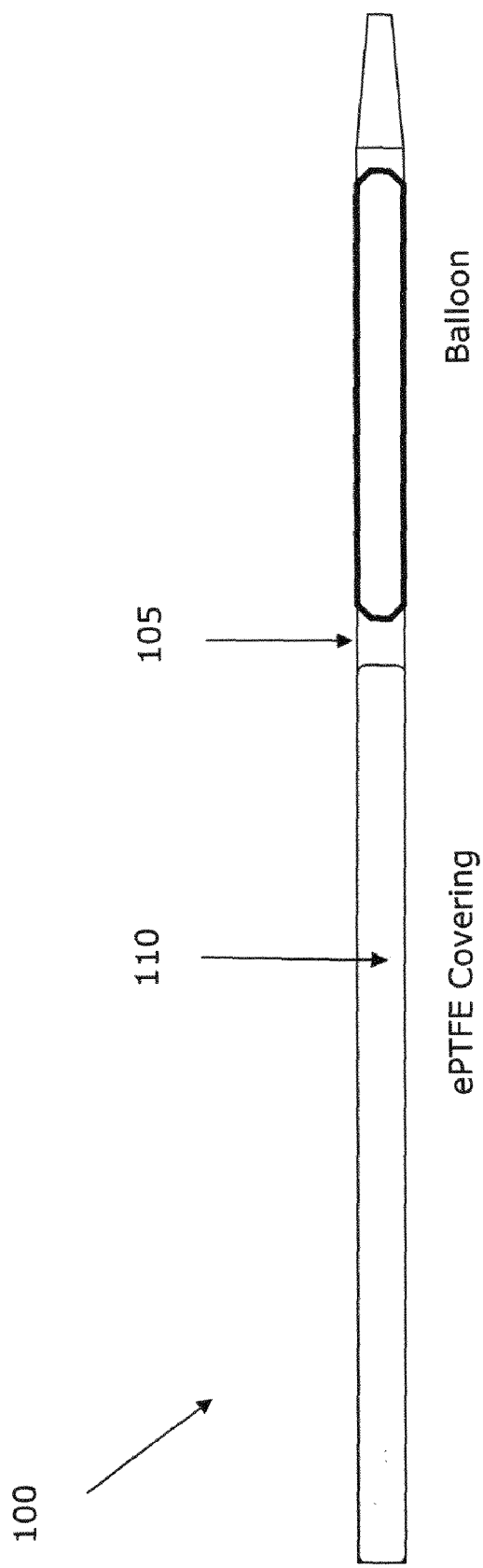
FIG. 1 is a schematic view of a novel catheter formed in accordance with the present invention.

As noted above, it has been found that a pure PFC solution, with or without a "passenger" gas saturation, cannot be safely injected directly into the arterial or venous bloodstream, e.g., using a standard intravenous (IV) line or syringe. This is because introducing pure PFC solutions in this manner creates dangerous embolisms in the blood. These embolisms are created due to the fact that the PFCs are hydrophobic and are not soluble in blood. Thus, when the PFC is injected directly into the bloodstream of a patient, the PFC tends to aggregate into relatively large bodies (or "particles") within the bloodstream. These relatively large aggregations of PFC tend to create embolisms in the bloodstream. For this reason, introducing pure PFCs (with or without a "passenger" gas) directly into the bloodstream of the patient, without using some sort of PFC-dispersing mechanism to "break up" the large PFC aggregations (or "particles"), is not feasible due to the creation of embolisms.

However, as also noted above, the use of emulsifiers as the PFC-dispersing mechanism introduces a whole new set of problems. Among other things, the use of emulsifiers as the PFC-dispersing mechanism can cause respiratory insufficiency and pulmonary edema, require the use of additional systemic oxygenation via the lung (with the associated risk of oxygen toxicity), and may cause allergic reactions.

Thus, a new PFC-dispersing mechanism is needed in order to permit a pure PFC solution (with or without "passenger" gas) to be safely and efficaciously introduced into the bloodstream.

The present invention provides a radically new (i.e., non-emulsifier) PFC-dispersing mechanism to permit the introduction of a pure PFC solution in the bloodstream while preventing the formation of large, embolism-inducing PFC aggregations in the bloodstream.

More particularly, the present invention employs a carefully constructed porous membrane (which may also be referred to as a porous substrate) to safely dispense pure, chemically inert PFCs directly into the bloodstream at sufficiently low rates, and in sufficiently small bodies, to prevent the creation of the aforementioned large PFC aggregations which lead to embolisms.

This carefully constructed porous membrane may be mounted on a catheter or wire or other device or intravascular structure (e.g., an atherectomy device, a stent, etc.); a pure PFC solution loaded into the porous membrane; and the catheter or wire or other intravascular device structure advanced into the vascular system of the patient so that the porous membrane is located at a selected site within the bloodstream; whereupon the porous membrane will act as a PFC-dispersing mechanism to dispense the pure PFC solution directly into the bloodstream—in a carefully controlled, highly dispersed manner—so that micro-, nano-, and subnano-sized quantities of PFC molecules safely enter the bloodstream, without the occurrence of large, embolism-inducing PFC aggregations. The pure PFC solution carries a sizable quantity of therapeutic gas (e.g., oxygen) therein, so that the gas-rich (e.g., oxygen-rich) PFC solution can deliver the therapeutic gas to downstream tissue (e.g., for oxygenation purposes).

An important aspect of the present invention is that the porous membrane must be carefully constructed so as to permit the gas-rich (e.g., oxygen-rich) PFC to enter the bloodstream at the appropriate rate. In fact, it has been discovered that it is important to form the porous membrane with a porosity which permits the gas-rich PFC to disperse into the bloodstream in very small volumes, and at a highly controlled rate which is both (i) sufficiently high to provide therapeutic benefit to the patient by the delivery of adequate quantities of therapeutic gas (e.g., oxygen) molecules to tissue, and (ii) sufficiently low so as to avoid the creation of embolisms in the bloodstream, even when using pure PFC solutions.

In practice, it has been discovered that, for a catheter or wire or other intravascular device or structure (e.g., atherectomy device, stent, etc.) placed into an artery having a typical rate of blood flow, forming the porous membrane with a porosity in the range of 0.001-200 microns, and preferably in the range of 20-200 microns, permits appropriate dispersion of the gas-rich PFC into the bloodstream without inducing embolisms.

It has also been discovered that a pore size of greater than 200 microns can increase the likelihood of creating embolisms in the bloodstream.

It has also been discovered that a pore size which is too small (e.g., less than 20 microns) can make it difficult to deliver enough gas molecules to a site to provide certain therapeutic benefits. Thus, for example, where it is desired to provide oxygenation therapy in larger diameter blood vessels, it may not be desirable to use a pore size of less than 20 microns, since this may not provide enough oxygen molecules to the downstream tissue. However, where the oxygenation therapy is to be provided in smaller blood vessels, or where some other, non-oxygenation therapy is to be provided to the patient, smaller quantities of therapeutic gas molecules may be adequate, in which case smaller pore sizes (e.g., 0.001 microns) may be satisfactory.

It has been discovered that, for oxygenation therapy, a pore size of 20-200 microns provides excellent therapeutic benefits while still preventing the creation of embolisms.

Construction Details

The present invention uses pure perfluorocarbon (PFC) as a media for delivering therapeutic gas molecules (e.g., $O_2$, NO, CO, etc., or any combination thereof) to cells at a target site. Although any PFC media may be used, PFO (perfluoro-n-octane) is preferred. As used herein, the term "pure PFC" is intended to mean a PFC solution with or without a gas therein, but which does not include emulsifiers therewith. Thus, the term "pure PFC" as used herein is intended to mean non-emulsified PFC. Furthermore, wherever the term "PFC" is used herein, it is intended to refer to pure (i.e., non-emulsified) PFC, unless it is otherwise stated.

The PFC is loaded with the desired therapeutic gas molecules (i.e., the "passenger" gas) until a certain percentage of saturation is achieved (preferably 100%). Preferably, the gas-rich (e.g., oxygen-rich) PFC is produced under normobaric or hyperbaric conditions at a production facility and then stored in a vial until use (e.g., until the gas-rich PFC is loaded into the porous membrane in the operating room).

As noted above, with prior art approaches, introducing a pure PFC solution (with or without gas molecules) directly into the bloodstream (e.g., via a needle) is not clinically acceptable due to the creation of dangerous embolisms. As also noted above, it is not practical to dilute the PFC with another liquid prior to injection, so as to reduce PFC aggregations in the bloodstream, due to the insoluble nature of the PFCs. Furthermore, as also noted above, it is not practical to use emulsifiers to disperse the PFCs within the bloodstream, since the use of emulsifiers can lead to problems of high fluid volume, less efficient oxygen delivery and possible allergic reactions.

The invention described herein overcomes these problems by dispensing a pure, chemically-inert PFC solution (with "passenger" therapeutic gas molecules carried therein) directly into the bloodstream, using a porous membrane (also sometimes referred to as a porous substrate) as a PFC-dispersing mechanism. The porous membrane dispenses the pure PFC solution directly into the bloodstream in a carefully controlled, highly dispersed manner so that micro-, nano-, and subnano-sized quantities of the PFC molecules enter the bloodstream. These tiny quantities of PFC molecules are small enough to avoid the creation of dangerous embolisms in the bloodstream.

Therefore, the present invention provides a unique approach for solving the aforementioned problems associated with prior art PFC delivery and makes it possible—for the first time—to clinically use a pure (i.e., non-emulsified) PFC solution to deliver a therapeutic gas (e.g., oxygen) to treat a medical condition (e.g., to prevent ischemia).

More particularly, the present invention provides a safe and effective way to deliver a gas-rich (e.g., oxygen-rich) PFC solution directly into the bloodstream, without the creation of embolisms, by loading the gas-rich PFC into a porous membrane which is part of a catheter or wire or other intravascular device or structure (e.g., atherectomy device, stent, etc.). The porous membrane is specifically constructed so that the PFCs elute out of the porous membrane, and are dispersed into the bloodstream, in a highly controlled manner, at a reproducible rate, and in small enough volumes, to avoid the creation of dangerous embolisms. This makes it practical, for the first time, to introduce a pure (i.e., non-emulsified) PFC solution directly into the bloodstream, without the risk of embolisms.

To this end, the porous membrane is formed out of a suitable porous material, e.g., Teflon, polyethylene, polyethylene terephthalate, nylon, silicon, cellulose acetate, etc. The porous material has a porosity which permits the gas-rich (e.g., oxygen-rich) PFC to be loaded into the porous membrane outside of the body and then, once the porous membrane is positioned in the bloodstream, to automatically disperse out of the porous material and into the bloodstream in very small volumes, and at a highly controlled rate which is both (i) sufficiently high to provide therapeutic benefit to the patient by the delivery of adequate quantities of therapeutic gas molecules to tissue, and (ii) sufficiently low so as to avoid the creation of fluid overload and/or embolisms in the bloodstream, even when using pure PFCs.

In practice, for oxygenation applications, forming the porous membrane with a porosity in the range of 20-200 microns has been found to permit appropriate dispersion of the oxygen-rich PFC into the bloodstream to adequately oxygenate tissue without causing embolisms. It has been found, however, that a pore size of >200 microns will tend to increase the likelihood of embolisms. Reducing the pore size of the porous membrane to the range of 0.001-20 microns further decreases the size of the PFC particles and hence further reduces the possibility of embolisms. However, it is believed that less PFC can be uploaded (per unit of membrane surface area, per unit of time) when the substrate is nanoporous and, in oxygenation applications, it may be necessary to use larger (e.g., 20-200 micron) pore sizes when the PFC is to be used to oxygenate tissue in larger diameter blood vessels. However, smaller pore sizes (e.g., 0.001-20 microns) may still be satisfactory when the PFC is being used to oxygenate tissue from within smaller diameter blood vessels, or when the therapeutic gas is something other than oxygen.

Further, it is believed that less PFC can be held in a porous membrane with smaller pore sizes than with a porous membrane with larger pore sizes. Thus, where substantial quantities of gas must be delivered to the tissue, and where it is desired to use smaller pore sizes, the overall surface area of the porous membrane may need to be increased, and/or the thickness of the porous membrane may need to be increased, in order to provide an adequate quantity of the therapeutic gas to the tissue.

Thus, a porous membrane formed with an appropriate pore size can be used to dispense the gas-rich (oxygen-rich) PFC into the bloodstream while limiting the size of the PFC aggregations within the bloodstream. For oxygenation applications, a pore size of 20-200 microns has been found to provide excellent therapeutic benefit while still preventing the creation of embolisms.

As noted above, the porous membrane (i.e., the porous substrate) preferably comprises an appropriate polymer. Teflon, polyethylene, polyethylene terephthalate, nylon, silicone, and cellulose acetate, etc. may all be used to form the porous membrane. The porous membrane preferably comprises a hydrophobic material which binds the hydrophobic perfluorocarbon (PFC) solution non-covalently via London forces (named after Fritz London, the German-American physicist). London forces are exhibited by non-polar molecules because electron density moves about a molecule probabilistically. The London forces become stronger with larger amounts of surface contact. Greater surface area contact means closer interaction between different molecules. A porous membrane with a porosity of between 0.001 and 200 microns, and preferably between 20 and 200 microns, offers a sufficient surface area, and is therefore ideal, for PFC applications where the PFC is to be released into the bloodstream in relatively small (i.e., non-embolism-causing) aggregations.

If the hydrophobic (non-polar) porous membrane is brought into contact with the hydrophobic (non-polar) perfluorocarbon (PFC) solution, the contact angle (e.g., wettability) of the pores of the porous membrane is 0°, which means that the PFC solution will be taken up by the porous membrane. In contrast, when the hydrophobic porous membrane is brought into contact with water or saline, the contact angle (e.g., wettability) is about 120°. The water or saline solution will therefore not be taken up by the hydrophobic porous membrane, and the perfluorocarbon (PFC) solution will not be diluted by other fluids, e.g., the water or saline solution.

The carefully-selected porosity of the hydrophobic polymer substrate (i.e., the porous membrane) allows the pure perfluorocarbon (PFC) solution to disperse into the bloodstream in PFC "particles" of micro, nano and sub-nano sizes. Forming the porous membrane out of polymers with a pore size of 0.001-200 microns, and preferably 20-200 microns, provides an effective incorporation of the gas-rich (oxygen-rich) perfluorocarbon (PFC) solution into the porous membrane, and provides a safe and effective rate of dispersion of the PFC solution into blood. A pore size above 200 microns increases the aggregation of the perfluorocarbon (PFC) molecules into the large aggregates that increase the likelihood of creating dangerous embolisms in blood. Therefore, a pore size above 200 microns is generally not preferred in the present invention.

Due to the construction of the porous membrane, predominantly nano- and micro-sized PFC aggregates (or "particles") are dispersed from the surface of the porous membrane into the bloodstream. In order to achieve a sufficient amount of oxygen delivery into blood so as to create a substantial hyperoxia in the blood for hyperoxic therapy, a sufficient amount of the nano- and micro-PFC particles have to be released from the surface of a catheter or wire or other intravascular device or structure (e.g., atherectomy device, stent, etc.) introduced into the bloodstream. Of course, many different catheter configurations, or wire configurations, or intravascular device or structure configurations, are possible, and many different porous membrane lengths (and/or surface areas) and porosities are possible, so it should be appreciated that variations and combinations of length (and/or surface area)/porosity/thickness may be employed in order to achieve the desired degree of gas deployment without the creation of embolisms. Furthermore, it should be appreciated that many different degrees of gas deployment may be desirable, depending on the therapeutic gas therapy which is to be effected (e.g., oxygenation or otherwise), the size of the blood vessel involved (e.g., larger or smaller), the quantity of tissue to be treated (e.g., oxygenated), etc.

In animal studies using a porous membrane to dispense a pure PFC solution carrying oxygen molecules, the actual pore size of the porous membrane was set to a mean size of 100 microns (range 20-200 microns). Animal studies in rabbits and pigs, studying the safety and efficacy of a catheter comprising a polymer membrane having a mean pore size of 100 microns (range 20-200 microns), clearly indicated that pores in the range of 20-200 microns are capable of delivering sufficient oxygen-rich perfluorocarbon (PFC) particles to blood so as to provide effective hyperoxic therapy. Moreover, in two different animal models of rabbits and pigs, no embolization of the PFC particles was detected in any of the studied animals. Pathology of pig hearts revealed that no perfluorocarbon (PFC) particles could be detected in the small arterioles and capillaries of the heart muscle (i.e., vessels of the end organ), and thus it was concluded that no embolization of the PFC particles had occurred during use of the inventive catheter in blood.

The amount (i.e., the quantity of molecules) of uptake of the gas-rich PFC solution into the porous membrane, and the amount (i.e., the quantity of molecules) of release of the gas-rich PFC solution from the porous membrane into the bloodstream generally depends on the length, the thickness and the porosity of the substrate membrane. The rate of release of the gas-rich PFC solution from the porous membrane into the bloodstream generally depends on the pore size of the porous membrane. Therefore, in order to induce adequate hyperoxic therapy with the present invention, e.g., elevating the oxygen tension of the blood for hyperoxic therapy without inducing embolisms, the pore size of the substrate (i.e., porous membrane) should preferably be in the range of 20-200 microns for blood vessels of a typical size.

The pore size required to achieve the desired rate of dispersion is effectively determined by the size of the PFC molecules, and is not dependent upon the type or concentration of the therapeutic gas molecules which are bound to the PFC. Thus, a catheter having a porous membrane with a porosity of 0.001-200 microns can be used to safely deliver PFC carrying substantially any therapeutic gas molecule (e.g., $O_2$, NO, CO, etc., or any combination thereof), at substantially any percentage of saturation (up to 100% saturation).

As noted above, in practice, it has been found that the pore size of the porous membrane governs the rate of release of the PFC from the catheter. Furthermore, it has been found that the surface area (i.e., length and circumference) and thickness of the porous membrane, together with the pore size, governs the total volume of PFC which may be carried by the device (and hence the total volume of the therapeutic "passenger" gas which may be carried by the medical device).

In one preferred form of the present invention, the porous membrane comprises multiple layers, with the multiple layers being deployed one on top of another.

And in one preferred form of the present invention, the porous membrane comprises multiple layers, with the porosity of the layers varying from one another. More particularly, in one preferred form of the present invention, the innermost layers of the porous membrane (i.e., those lying closest to the center axis of the catheter or wire or other intravascular device or structure) comprise relatively large pore sizes so as to accommodate relatively large amounts of PFC and so as to release that PFC to the outermost layers of the porous membrane as rapidly as the PFC may be accepted by the outermost layers of the porous membrane. At the same time, however, it is preferred that the outermost layers of the porous membrane (i.e., those contacting the bloodstream) be provided with smaller pore sizes (e.g., in the range of 0.001-200 microns, and preferably in the range of 20-200 microns) so as to control the rate of release of the PFC from the catheter in order to avoid the creation of dangerous embolisms.

At the time of use, the catheter (or wire or other intravascular device or structure) is immersed in a vial of gas-rich PFC so that its porous membrane is loaded with the gas-rich PFC, similar to how a sponge is loaded with water. The catheter (or wire or other intravascular device or structure) is then inserted into the vascular system of the patient. Due to the carefully selected porosity of the porous membrane, the gas-rich PFC then elutes out of the porous membrane and disperses into the patient's bloodstream at a rate which limits aggregations of the gas-rich (e.g., oxygen-rich) PFC within the bloodstream to a relatively small size, e.g., 0.001-200 microns. This controlled dispersion of the gas-rich PFC from the porous membrane into the bloodstream prevents embolisms from occurring while still providing sufficient quantities of the therapeutic gas (e.g., oxygen) molecules to provide the desired treatment to the patient. In other words, the porous membrane is carefully engineered so as to elute the gas-rich (e.g., oxygen-rich) PFC at a rate which effectively disperses the PFC in the bloodstream so as to avoid the creation of embolisms. Thus, the present invention permits the direct introduction of pure PFC solutions into the bloodstream, without requiring the use of emulsifiers to avoid the creation of embolisms (and hence without the aforementioned disadvantages associated with the use of emulsifiers).

As the gas-rich PFC travels downstream, most of the gas molecules remain attached to the PFC. Some of the gas molecules may also be released from the PFC into the blood. The gas molecules which are released from the PFC into the blood may or may not be picked up by various blood components (e.g., hemoglobin).

At the target tissue site, the gas (e.g., oxygen) molecules bound to the PFC are released to the cells of the patient's tissue. It will be appreciated that the manner in which the gas molecules are released from the PFC is dependent upon both the hemodynamics of the blood environment and time, in much the same way that oxygen molecules are normally released from the blood components of the patient.

More particularly, the gas-rich PFC enters the target tissue region. Due to the fact that the gas (e.g., oxygen) concentration ("tension") in the cells is lower than the gas (e.g., oxygen) concentration ("tension") in the capillary blood, the gas-rich PFC releases the therapeutic gas (e.g., oxygen) molecules. The therapeutic (e.g., oxygen) molecules can then enter the cells of the patient's tissue.

At the target tissue site, the PFC molecules are also available to pick up waste materials (e.g., gases such as carbon dioxide) and carry those waste materials away from the target site, in essentially the same manner that hemoglobin carries away waste materials from the cells. More particularly, the carbon dioxide ($CO_2$) level increases after cellular activity, and therefore the $CO_2$ concentration ("tension") in the cells is higher than the $CO_2$ concentration ("tension") in the capillary blood. As a result, the $CO_2$ molecules move from the cells into the capillary blood and become attached to the "gas-poor" PFC, which has previously given up its "passenger" gas (e.g., oxygen) to the cells. The PFC, now loaded with $CO_2$, enters the venous bloodstream and is transported to the lungs, where the $CO_2$ is expelled from the body.

It should also be appreciated that the PFC solution incorporated in the porous membrane need not necessarily carry a therapeutic gas. More particularly, where the primary concern is to remove waste materials (e.g., carbon dioxide) from tissue, the PFC solution loaded into the porous membrane may not be loaded with, or at least may not be completely saturated with, a therapeutic gas. In this case, the gas-poor PFC solution (which is still released safely from the porous membrane without the creation of embolisms) can pick up waste materials (e.g., carbon dioxide) at the tissue and carry it downstream for purging (e.g., by the lungs).

The present invention may be incorporated in various medical devices, in the form of various embodiments, according to the therapy which is to be provided to the patient.

More particularly, in one form of the present invention, there is provided a therapeutic gas delivery apparatus (e.g., a catheter or wire or other intravascular device or structure) for the treatment of disorders (e.g., cardiovascular diseases) that allows the local diffusion of a gas-rich (e.g., oxygen-rich) PFC solution into blood (and/or tissue), whereby to deliver that gas to the blood (and/or tissue). The invention is characterized by a porous membrane which is part of an appropriate medical device, with the porous membrane being impregnated with a gas-loaded (e.g., $O_2$, NO, CO, etc.) perfluorocarbon (PFC) solution, e.g., by the application of a heating or cooling solution, or by utilizing heating or cooling apparatus such as resistance heaters, thermoelectric heaters and/or coolers, etc.).

The release kinetics of the PFC solution from the porous membrane may be modulated by controlled temperature changes of the environment. In other words, the rate of release of the PFC solution from the porous membrane may be modulated by heating or cooling the PFC solution and porous membrane.

The PFC-impregnated porous membrane is preferably sealed in a protective housing made of plastic or metal, allowing the medical device to be pre-loaded with the gas-rich (e.g., oxygen-rich) PFC solution and then stored without the loss of the therapeutic gas and/or the gas-carrying PFC solution.

One of the goals of the present invention is to improve oxygen supply to ischemic organs during an angioplasty procedure. For instance, the present invention may be used to prolong balloon inflation times during high-risk PTCA procedures such as balloon or stent treatment of the trunk of the left main coronary artery. Moreover, the present invention may be used to reduce the extent of acute or subacute myocardial infarction and ischemic stroke. The gas-rich PFC prevents cell death by providing oxygen and other gases, such as nitric oxide (NO) and/or carbon monoxide (CO), thereby preventing excessive inflammation of an organ's tissue. This can be particularly true in infarctions with massive inflammation occurring as a response to tissue damage, where adding small amounts of nitric oxide (NO) and/or carbon monoxide (CO) to oxygen may reduce the negative effects of inflammatory cells such as neutrophils and macrophages. In other words, where infarctions have massive inflammation, providing a PFC solution rich in oxygen and smaller amounts of nitric oxide (NO) and/or carbon monoxide (CO) can have substantial therapeutic benefit.

Furthermore, in another embodiment characterized by a setting of cardiac arrest, the present invention may be used to oxygenate the body via the endovascular approach while chest compressions are performed. Thus, the body will be oxygenated without a ventilation of the lung during the resuscitation.

Furthermore, the invention disclosed herein may be utilized to reduce restenosis following an angioplasty procedure.

The invention disclosed herein presents a novel approach for an angioplasty procedure (including a stent implantation) by improving not only the acute safety of the procedure but also the long-term outcome of the procedure.

In a similar manner, the present invention also may be used to prolong procedure times for plaque removal procedure times with atherectomy devices, for example, atherectomy devices that use mechanical blades or laser energy as a means to extract or ablate atherosclerotic plaque within an artery.

A major aspect of the present invention is the local delivery of oxygen (or other therapeutic gases) into blood (and/or tissue) via a perfluorocarbon (PFC) solution delivered via a percutaneously deliverable device. In addition, with the present invention, the local delivery of oxygen (or other therapeutic gases) can be achieved without requiring the use of software, electronic equipment, or mechanical pumping equipment or hardware (e.g., pumps, chambers, computers, bubble detectors, etc.). The gas-rich (e.g., oxygen-rich) PFC is released to the target area from a porous membrane carried by a catheter (e.g., a tube catheter, a balloon catheter, a perfusion balloon catheter, etc.) or a wire (e.g., a coronary wire, a guidewire, etc.) or other intravascular device or structure (e.g., an atherectomy device, a stent, etc.).

The apparatus presented herein allows for the local diffusion of an oxygen-rich PFC solution into hypoxic target tissues, where oxygen is safely released from the PFC into the bloodstream and increases the oxygen tension of the target tissue.

A porous membrane is used to releasably hold the gas-rich PFC on the device. Preferably the porous membrane comprises a polymer. During the manufacture of the porous membrane polymer, the porosity of the basic polymer material is induced in the range of 0.001-200 microns, and preferably in the range of 20-200 microns.

The porous membrane may be formed as an integral part of an appropriate medical device, or it may be securely attached to the medical device, or it may be securely attached to another component which is itself attached to the medical device.

In addition, a surface or portion of the catheter or wire or other intravascular device or structure which itself comes in contact with the bloodstream may be manufactured (e.g., etched or chemically treated) so as to induce the desired porosity on such surface or portion of the catheter or wire or other intravascular device or structure, so as to create the desired porosity in the range of 0.001-200 microns in order to releasably hold and safely disperse the gas-rich (e.g., oxygen-rich) PFC. It should be noted that a catheter and/or wire and/or other intravascular device or structure with a surface so treated so as to create the desired porosity may also be configured so as to further incorporate a porous membrane(s) within one or more lumens of the catheter or wire or other intravascular device or structure.

It is disclosed herein that the microporous material is carried by a medical device, and the medical device is impregnated with a gas-rich (e.g., oxygen-rich) PFC solution. Perfusion channels carrying liquids around the medical device may also be provided to allow the perfusion of warm and/or cold liquids so as to modulate the release of the gas-rich (e.g., oxygen-rich) PFC from the porous membrane. These induced local temperature changes modulate (i.e., increase or decrease) the rate of release of the PFC solution from the porous membrane, whereby to modulate the rate of delivery of the therapeutic gas (e.g., oxygen) molecules to the tissue.

Polymer tubes formed out of a porous structure and/or incorporating a porous material, and impregnated with oxygenated perfluorocarbon (PFC) solutions, may be used to supplement oxygen delivery to the blood during a cardiopulmonary bypass procedure.

Modified stent delivery catheters, (e.g., balloon catheters with a pre-mounted stent), and/or perfusion balloon catheters, and/or wires (e.g., cardiac wires, guidewires, etc.) and/or arterial plaque-removing atherectomy devices, and/or other intravascular devices or structures are all among the preferred embodiments of the invention. The porous membrane may be dispersed substantially anywhere on the medical device, including on an outer surface of the device, an interior surface of the device, and on the outer surface of any balloon carried by those devices. Endovascular stents themselves may also be coated with a thin film porous membrane which incorporates the gas-rich (e.g., oxygen-rich) perfluorocarbon (PFC) solution.

For restenosis prevention, the local delivery of a oxygenated perfluorocarbon (PFC) solution may be combined with the application of ionizing radiation or low energy ultraviolet light so as to increase the production of oxygen free radicals in the target cell of an arterial wall. The effect of increased oxygen free radical production on the proliferating target cell in the arterial wall is DNA damage, which will cause a reduction of restenosis formation.

A therapeutic device that provides local tissue oxygenation may also be applied to other fields of vascular medicine. By way of example but not limitation, wound healing of skin in patients with peripheral occlusive arterial disease and impaired blood flow in the lower limb organs may be significantly improved with the local delivery of an oxygenated perfluorocarbon (PFC) solution via a skin patch placed onto the ischemic skin, where the skin patch includes the porous membrane therein. These oxygenated tissue patches promote the growth of new blood vessels into the area of ischemia, for instance in surgically-opened wounds. Gangrenes of the lower limb due to arteriosclerosis may be reduced in size through the use of the present invention.

By way of example but not limitation, the tissue patch carrying the gas-rich PFC solution may be incorporated in a bandage or other wound dressing.

In addition, these skin patches can deliver therapeutic gases in addition to oxygen.

Furthermore, these oxygenated tissue patches can be used to oxygenate tissue other than skin. By way of example but not limitation, these oxygenated tissue patches can be used to topically apply a gas-rich (e.g., oxygen-rich) PFC to internal tissues (e.g., the intestines), whereby to supply a therapeutic gas (e.g., oxygen) to such tissues.

Thus, in one form of the present invention, there is provided a tissue patch for delivering a therapeutic gas to tissue, wherein the tissue patch comprises a porous membrane which is impregnated with a gas-rich PFC solution.

In another preferred embodiment of the present invention, the porous membrane is located on the surface of a balloon of an angioplasty catheter. The porous membrane comprises a porous polymer, preferably at a thickness of between 0.5-4 mm (and most preferably at a thickness of between 0.6-1.4 mm). Among other things, the thickness of the porous membrane may be constrained by the inner diameter of the guiding catheter used, i.e., in the case of coronary and cerebal artery guiding catheters, the limit of membrane thickness might typically be in the range of 1-2 mm. The porous membrane can be integrated into the balloon, and/or into the catheter shaft structure, or can be wrapped around the balloon and/or the catheter shaft structure. The thin film porous polymer membrane is impregnated with an oxygenated perfluorocarbon (PFC) solution. The porous membrane is preferably sealed within a housing so as to prevent premature release of the gas-rich PFC (and/or the therapeutic gas itself). Prior to the intended angioplasty procedure, the housing is removed from the medical device, and the medical device is then advanced into the bloodstream. At the target site, the porous membrane may be brought into contact with the vessel wall. The release kinetics of the gas-rich PFC may also be modified by changes of local temperature between about 0 degrees Celsius and 50 degrees Celsius, e.g., by the injection of cold and/or warm fluids via the guiding catheter prior to inflation of the balloon. The oxygen enters the blood vessel wall by diffusion. Direct contact of the medical device with the target tissue typically improves oxygen delivery. The local increase in oxygen molecules creates an excess of oxygen free radicals when either (i) ionizing radiation with beta-particle emitters (such as Sr-90/Y-90 or P-32) is applied to the target area, or (ii) ultraviolet light is applied to the target area. A simultaneous application of the oxygenated PFC solution with vessel irradiation (using ionizing radiation or ultraviolet light) is the preferred treatment modality for restenosis prevention.

The oxygen saturation of an end organ increases with improved oxygenated blood flow. Therefore, in another embodiment of the present invention, the oxygenated PFC is released from a perfusion balloon catheter. The perfusion balloon catheter provides for the flow of blood from the proximal end of the occluding balloon into the vascular bed distal to the occluding balloon (i.e., blockage), and thus increases the distribution of the oxygenated perfluorocarbon (PFC) solution to the end organ. Perfusion of blood through the occluded balloon is permitted, and the blood is oxygenated at the proximal end of the balloon, upstream of the balloon (i.e., upstream of the blood flow blockage), so that the oxygenated blood can flow past the balloon to the tissue.

In yet another embodiment of the present invention, the oxygenated PFC is delivered from a porous membrane which is part of a flexible coronary wire or other medical wire device or structure. In a preferred embodiment, the metallic wire is in the form of a flexible hypo-tube, whereby the wire has a lumen that extends from its proximal end through to the distal tip. The porous membrane, which carries the gas-rich PFC solution, is configured such that the porous membrane is positioned inside the lumen, and can extend within a portion of the lumen or from the proximal end all the way to the distal tip of the metallic wire. For example, the porous membrane could be modified to form a thread-like structure or structures. The gas-rich PFC solution is introduced into the porous membrane from the proximal end of the metallic wire through a delivery mechanism (e.g., including but not limited to a syringe) in the appropriate dose or dosages. In addition, the gas-rich PFC solution could be introduced into the porous membrane by a means providing for continuous delivery, which can be a powered device (e.g., including but not limited to an infusion pump) or a passive device (e.g., including but not limited to a gravity-fed drip, much like how a intravenous solution is infused from an IV bag). Then, as the porous membrane is loaded with the liquid oxygen carrier (i.e., the gas-rich PFC) at the proximal end of the metallic wire, capillary action enables the absorption of the gas-rich PFC from the proximal portion of the modified porous membrane through to the distal end of the modified porous membrane, much like dipping the proximal end of a strip of dry facial tissue into water and watching the water being absorbed up into the tissue to the distal end of the strip of tissue. Then, at the tip of the metallic wire where the distal end of porous membrane terminates, the release kinetics of the gas-rich PFC into the bloodstream (as described herein) draws the gas-rich PFC from the porous membrane at the tip of the flexible hypo-tube wire and into the bloodstream. Thus, the gas-rich PFC can be impregnated throughout the length of the modified porous membrane contained within the internal lumen of the wire and then be dispersed out the tip of the flexible metallic wire and into the blood stream, either in dosages or via a continuous flow, at rates which are both (i) sufficiently high to provide therapeutic benefit of the delivery of adequately high therapeutic gas molecules to tissue, and (ii) sufficiently low so as to avoid the creation of fluid overload and/or large particle embolisms in the bloodstream.

In a similar manner, the membrane carrying the liquid perfluorocarbon (PFC) solution can be modified such that the oxygen carrier membrane forms a tube around a retrievable metallic core that is positioned within the wire lumen. The wire containing the core within it can be advanced beyond the lesion (i.e., coronary obstruction) in the distal coronary artery. Then, as the core holding the porous membrane tube within the wire is held at a fixed position, the wire can be retracted an appropriate distance to expose the tube-shaped carrier membrane so as to allow the tube carrying the oxygen source (i.e., the oxygen-rich PFC solution) to dwell in the bloodstream. Thereafter, in all of the aforementioned flexible wire embodiments, a conventional balloon catheter can be advanced over the wire to a treatment zone preferentially proximal to the oxygen delivery source. These aforementioned embodiments permit prolonged balloon inflation as a result of allowing simultaneous oxygen delivery distal to the lesion during balloon inflation, thus eliminating the risk of myocardial ischemia during balloon inflation. Additionally, supplemental oxygen can continue to be delivered after balloon inflation. It should be noted that it may be desirable to advance a balloon catheter over the wire to a treatment zone distal to the oxygen delivery source, depending on the anatomical structure of the blood vessels, so as to allow dispersement of gas-rich PFC before and after balloon inflation.

In yet another embodiment, the distal tip of a coronary wire is coated with the porous membrane carrying the liquid perfluorocarbon (PFC) solution. Alternatively, the porous membrane carrying the gas-rich PFC solution is modified such that the porous membrane forms a tube around the wire. The wire is placed in the distal coronary artery, and the porous membrane is allowed to dwell in the bloodstream so as to dispense the gas-rich PFC solution into the bloodstream. Thereafter, a conventional balloon catheter can be advanced over the wire to a treatment zone, which may be proximal or distal to where the gas-rich PFC was released. If desired, the tubular porous membrane can be withdrawn from the wire prior to advancing the balloon catheter over the wire, or the balloon catheter can be advanced over the tubular porous membrane. In either case, this approach permits prolonged balloon inflation without inducing myocardial ischemia.

In some cases it may be preferably to place the porous membrane inside of the lumen of a guidewire. For oxygen delivery, a length of ePTFE "tubing" is placed inside the wire lumen. Because the wire may be designed with an 0.014" outer diameter (which is a typical maximum outer diameter of a coronary wire), it may not always be possible to place the ePTFE tube on the outside of the wire in the case where an angioplasty catheter is to be advanced over the wire. Note that a huge clinical advantage can be obtained where a catheter is to be advanced over an oxygen-delivering wire, thus simultaneously providing balloon dilatation and oxygenation delivery distal to the obstruction.

In yet another embodiment of the present invention, the wire is porous. The wire is impregnated with the gas-rich PFC at its distal tip or along its length.

In yet another embodiment of the present invention, the distal tip of the wire forms a plastic thread which is tightly connected to the metallic portion of the wire.

Illustrated Embodiments

Figure 3:
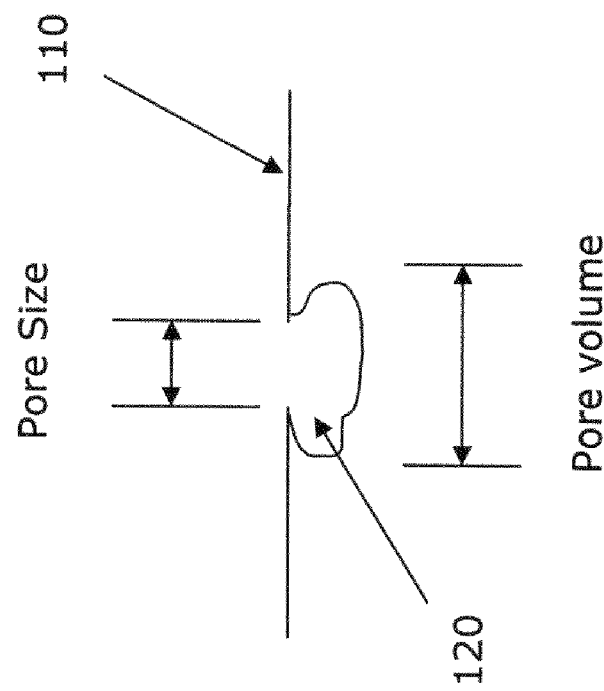
FIGS. 2 and 3 are schematic views illustrating the porous membrane of the novel catheter of FIG. 1, and how the gas-rich (e.g., oxygen-rich) PFC elutes out of the porous membrane.
Figure 2:
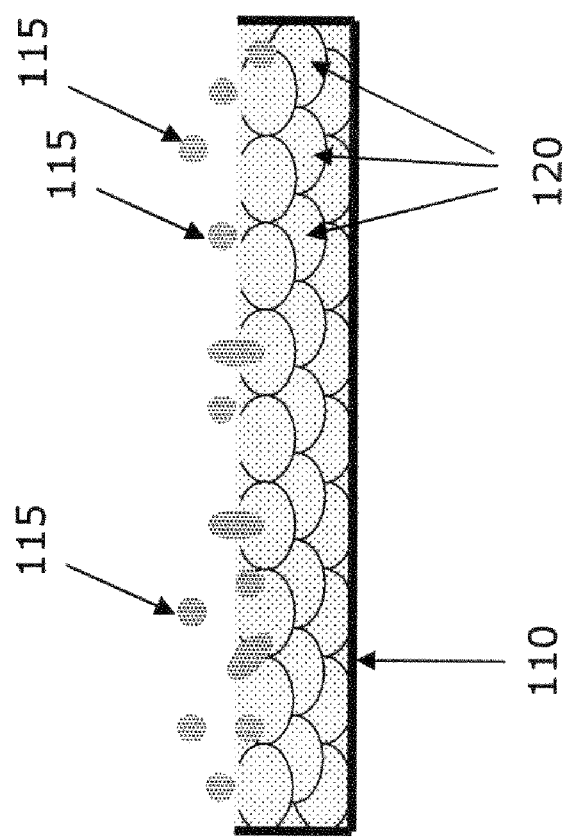

Looking now at FIGS. 1-3, there is shown a catheter 100 which comprises a shaft 105 comprising a porous membrane 110. Porous membrane 110 is saturated with a gas-rich (e.g., oxygen-rich) PFC solution 115 which is contained in pores 120 formed in porous membrane 110. Porous membrane 110 is preferably formed out of a polymer (e.g., Teflon, polyethylene, polyethylene terephthalate, nylon, silicone, cellulose acetate, etc.). Porous membrane 110 is formed with a porosity which permits gas-rich PFCs to be loaded into the porous membrane and thereafter to be dispersed into the bloodstream at a rate which is both (i) sufficiently high to provide therapeutic benefit by the delivery of a sufficient quantity of gas molecules to tissue, and (ii) sufficiently low so as to avoid the creation of fluid overload and/or large PFC-particle embolisms in the bloodstream.

In practice, for a catheter placed into an artery having a typical blood flow, forming the porous membrane with a porosity in the range of 0.001-200 microns has been found to permit appropriate dispersion of the gas-rich PFC into the bloodstream. However, it has also been found that a pore size of >200 microns will increase the likelihood of embolisms. Thus, it is desired to keep the pore size in the range of 0.001-200 microns. This pore size tends to limit gas-rich PFC aggregations within the bloodstream to a very small size, e.g., 0.001-200 microns, which has been found to provide therapeutic benefit while still preventing the creation of embolisms. For oxygenation applications, the porous membrane preferably has a pore size in the range of 20-200 microns.

The pore size required to achieve the desired rate and volume of PFC dispersion is effectively determined by the size of the PFC molecules, and is not dependent upon the type or concentration of the therapeutic gas molecules which are bound to the PFC. Thus, a catheter having a porous membrane with a porosity of 0.001-200 microns can be used to deliver PFCs carrying substantially any therapeutic molecule (e.g., $O_2$, NO, CO, etc., or any combination thereof), at substantially any percentage of saturation.

Looking now at FIGS. 4-7, at the time of use, the catheter 100 is immersed in a vial 125 of pure, gas-rich PFC so that the porous membrane is loaded with the gas-rich PFC, in a manner similar to how a sponge is loaded with water.

Looking next at FIG. 8, catheter 100 (preferentially a monorail balloon catheter or a stent delivery balloon catheter) is then inserted into the vascular system (e.g., blood vessel 130) of the patient, so that porous membrane 110 comes into contact with the patient's blood 135. Due to the carefully selected porosity of porous membrane 110, gas-rich PFC 115 is dispersed out of the porous membrane and into the bloodstream of the patient at a rate which limits aggregations of the gas-rich PFC to a very small size, e.g., one which avoids the creation of embolisms even when using pure (i.e., non-emulsified) PFC. It is this controlled release of the gas-rich PFC from the porous membrane which prevents embolisms.

As the gas-rich PFC travels downstream, most of the gas molecules remain attached to the PFC molecules. Some of the gas molecules, however, may also be released from the PFC molecules into the blood. The gas molecules which are released from the PFC molecules into the blood may or may not be picked up by hemoglobin or other blood components.

At the target tissue site, the gas molecules bound to the PFC are released to the cells. It will be appreciated that the manner in which the gas molecules are released from the PFC is dependent upon both the hemodynamics of the blood environment and time, in much the same way that oxygen is normally released from hemoglobin.

More particularly, gas rich PFC enters the target tissue region. Due to the fact that oxygen tension in the cells is lower than the oxygen tension in the capillary blood, the oxygen-rich PFC releases its oxygen molecules. The oxygen molecules can then enter the cells.

At the target site, PFC molecules are also available to pick up waste materials (e.g., gases such as $CO_2$) and carry them away from the target site, in essentially the same manner that hemoglobin carries away waste materials from cells. More particularly, the $CO_2$ level increases in a cell after cellular activity, and therefore the $CO_2$ tension in the cells is higher than the $CO_2$ tension in the capillary blood. The $CO_2$ molecules move from the cell into the capillary blood and become attached to the "gas-poor" PFC (which has previously given up its oxygen). The PFC, now loaded with $CO_2$, enters the venous bloodstream and is transported to the lungs, at which time the $CO_2$ is expelled.

It should also be appreciated that the PFC solution incorporated in the porous membrane need not necessarily carry a therapeutic gas. More particularly, where the primary concern is to remove waste materials (e.g., carbon dioxide) from tissue, the PFC solution loaded into the porous membrane may not be loaded with, or at least may not be completely saturated with, a therapeutic gas. In this case, the gas-poor PFC solution (which is still released safely from the porous membrane without the creation of embolisms) can pick up waste materials (e.g., carbon dioxide) at the tissue and carry it downstream for purging (e.g., at the lungs).

Still looking now at FIG. 8, to the extent that catheter 100 is formed with a balloon 140, the balloon may be inflated as shown in FIG. 9, e.g., so as to dilate the vessel and/or to set a stent. It will be appreciated that as the balloon is inflated, the blood vessel may be occluded. However, inasmuch as the tissue downstream of the balloon has previously been super-oxygenated with oxygen-rich PFC delivered by in-dwelling catheter 100 prior to balloon inflation, longer periods of occlusion, with less detrimental results, may be achieved. Alternatively, and/or additionally, shaft 105 of catheter 100 may be cannulated so as to provide an oxygen delivery catheter, whereby to permit blood flow through the catheter even when the balloon is inflated.

Thereafter, as shown in FIG. 10, balloon 140 may be deflated, whereby to permit continued delivery of gas-rich PFC, removal of waste materials (e.g. $CO_2$), and the withdrawal of catheter 100 from blood vessel 130.

Significantly, in one preferred form of the present invention, catheter 100 can be placed into a blood vessel and left to dwell there for several minutes before balloon inflation, whereby to permit the tissue downstream of the lesion to be pre-conditioned with a supply of PFC-delivered oxygen. As a result, when the balloon is subsequently inflated, the patient can tolerate "standard" balloon inflation times with less or no pain. In addition, longer periods of balloon inflation can be achieved with less risk of ischemia, less risk of tissue damage, and less risk of arrhythmias that otherwise could result due to hypoxia.

Furthermore, after balloon deflation, the catheter can be maintained in position within the blood vessel so as to continue to deliver oxygen-rich PFC to the downstream tissue and remove waste materials (e.g. $CO_2$), so as to extend the therapeutic event.

If desired, balloon 140 (and preferentially a so-called "Rapid Exchange", or stent delivery, balloon) may be omitted from shaft 105 of catheter 100.

Figure 11:
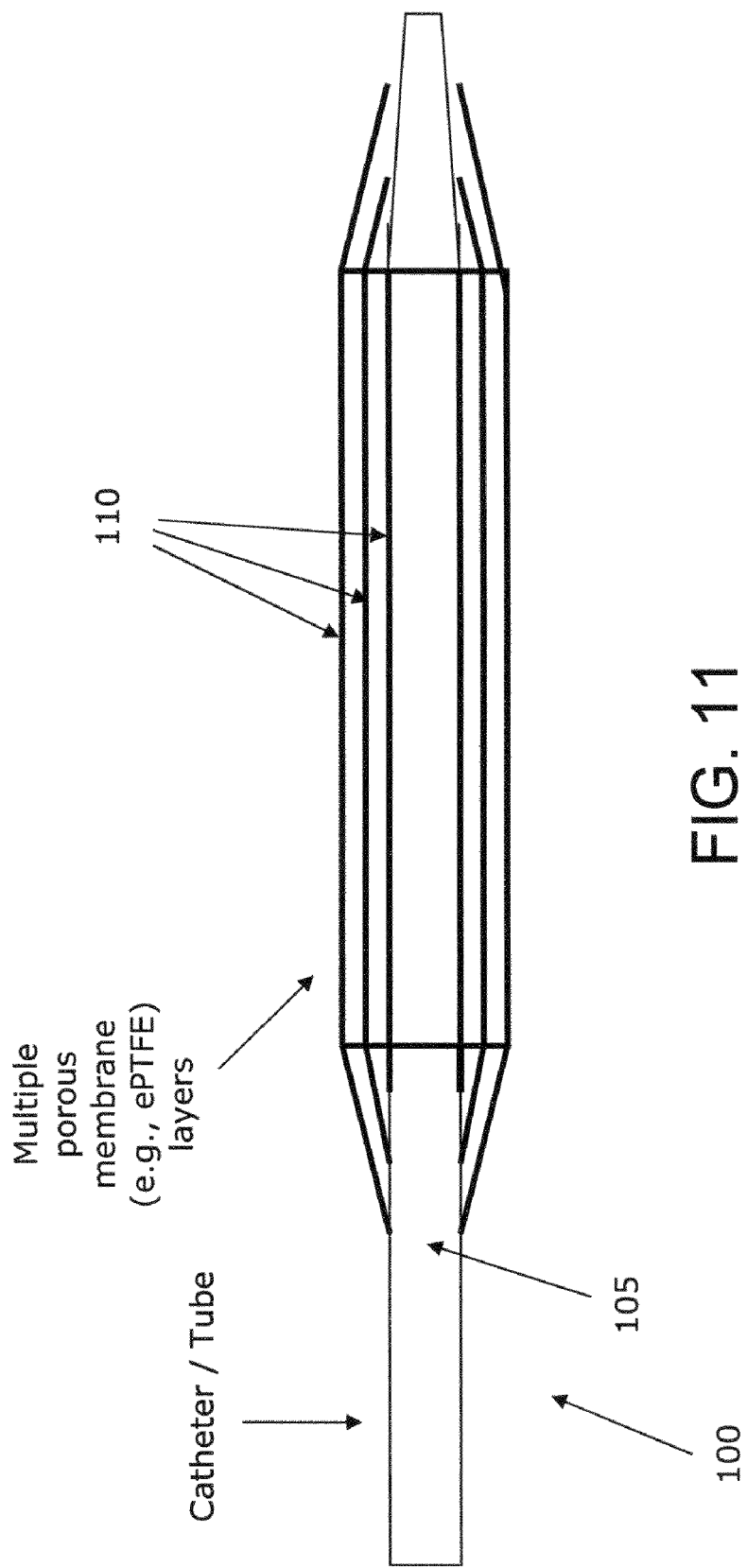
FIG. 11 is a schematic view showing another catheter formed in accordance with the present invention, wherein the catheter comprises multiple layers of porous membrane.
Figure 12:
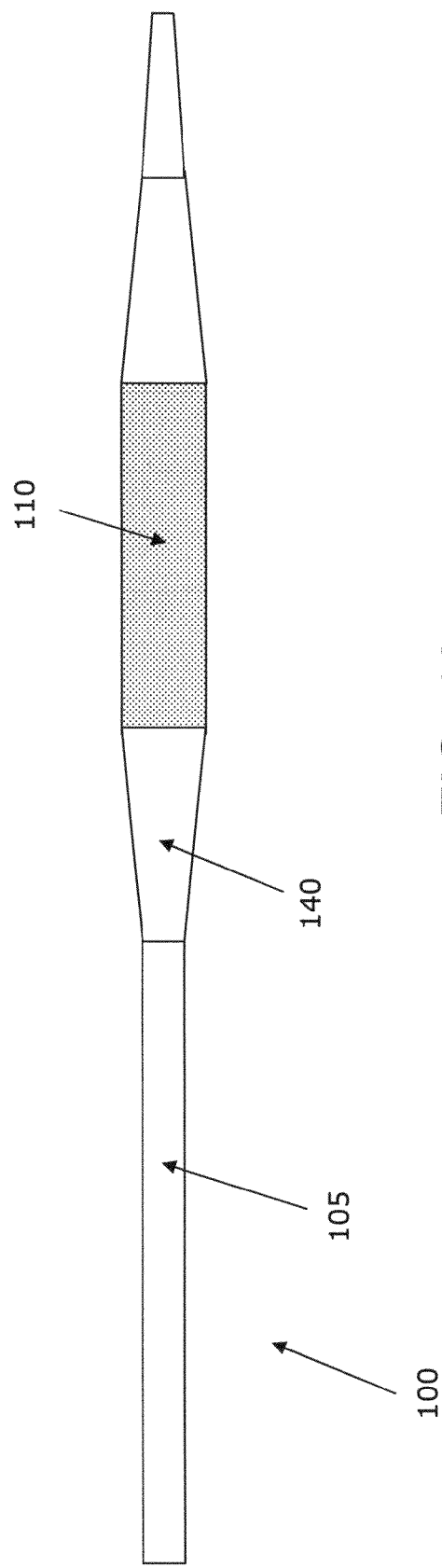
FIGS. 12-16 are schematic views showing a balloon catheter formed in accordance with the present invention, and how it may be used to apply gas-rich (e.g., oxygen-rich) PFC directly to the walls of a blood vessel.
Figure 13:
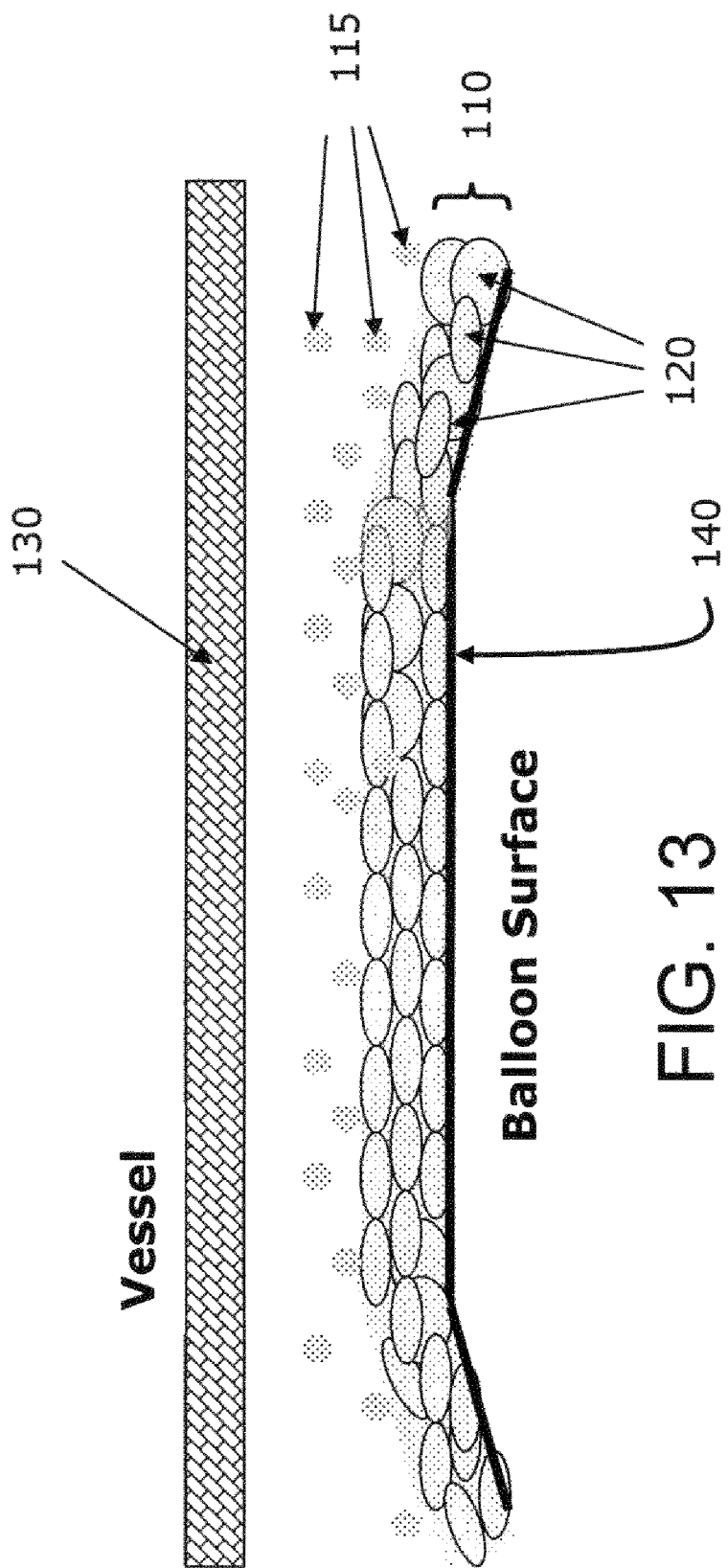
Figure 14:
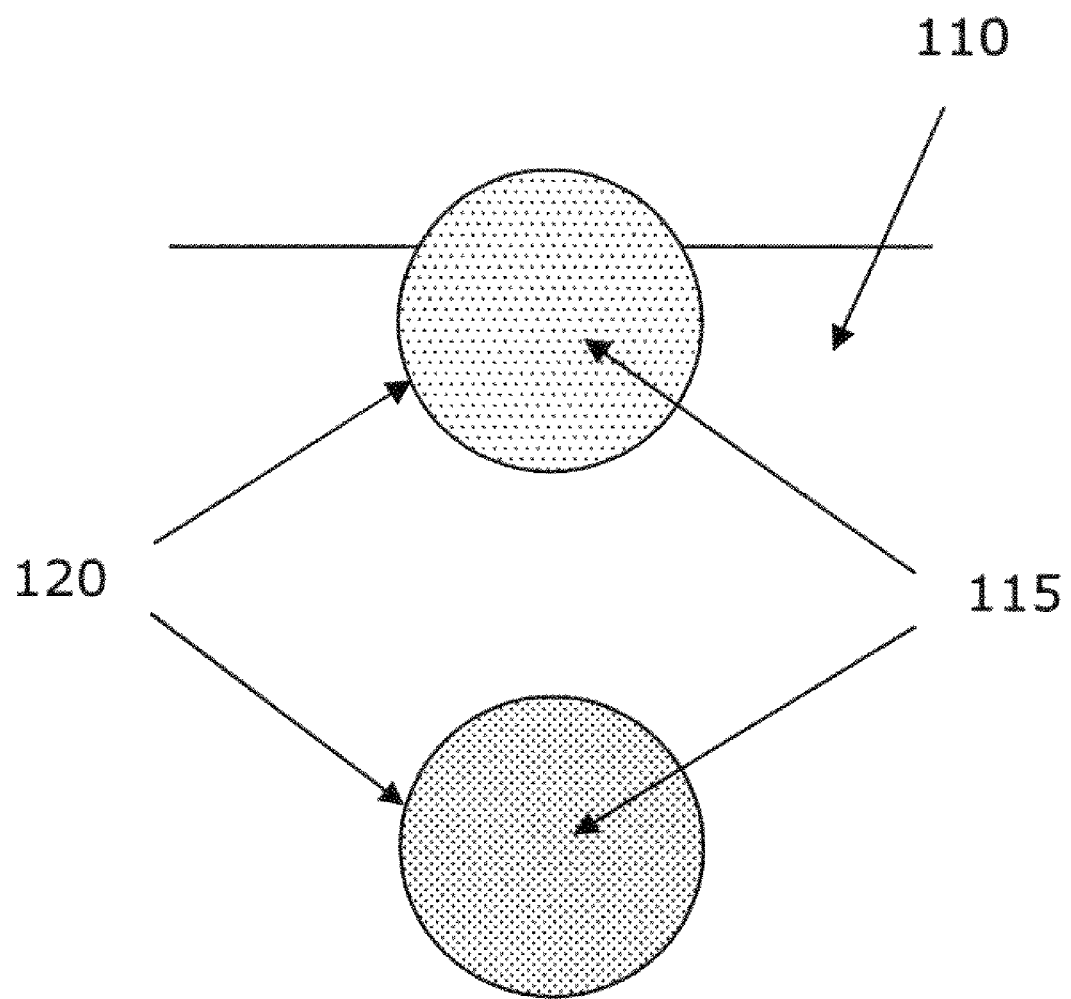
Figure 15:
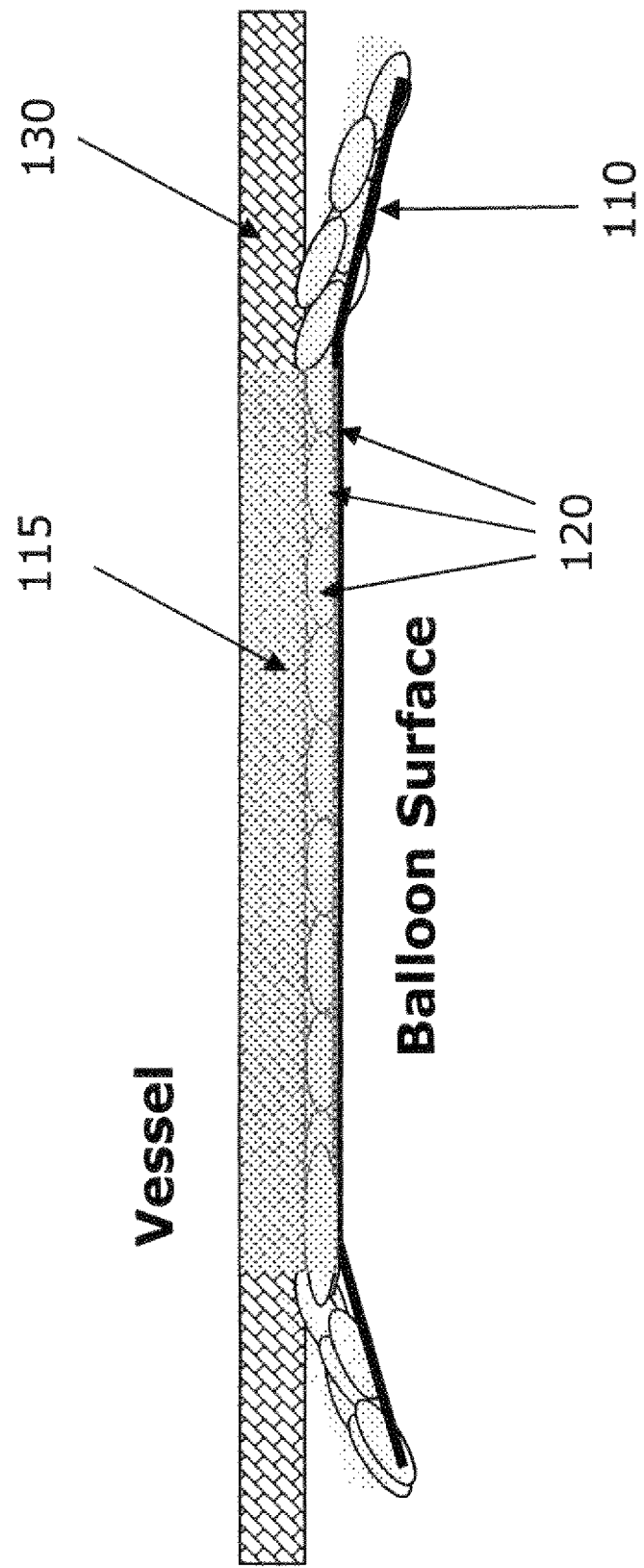
Figure 16:
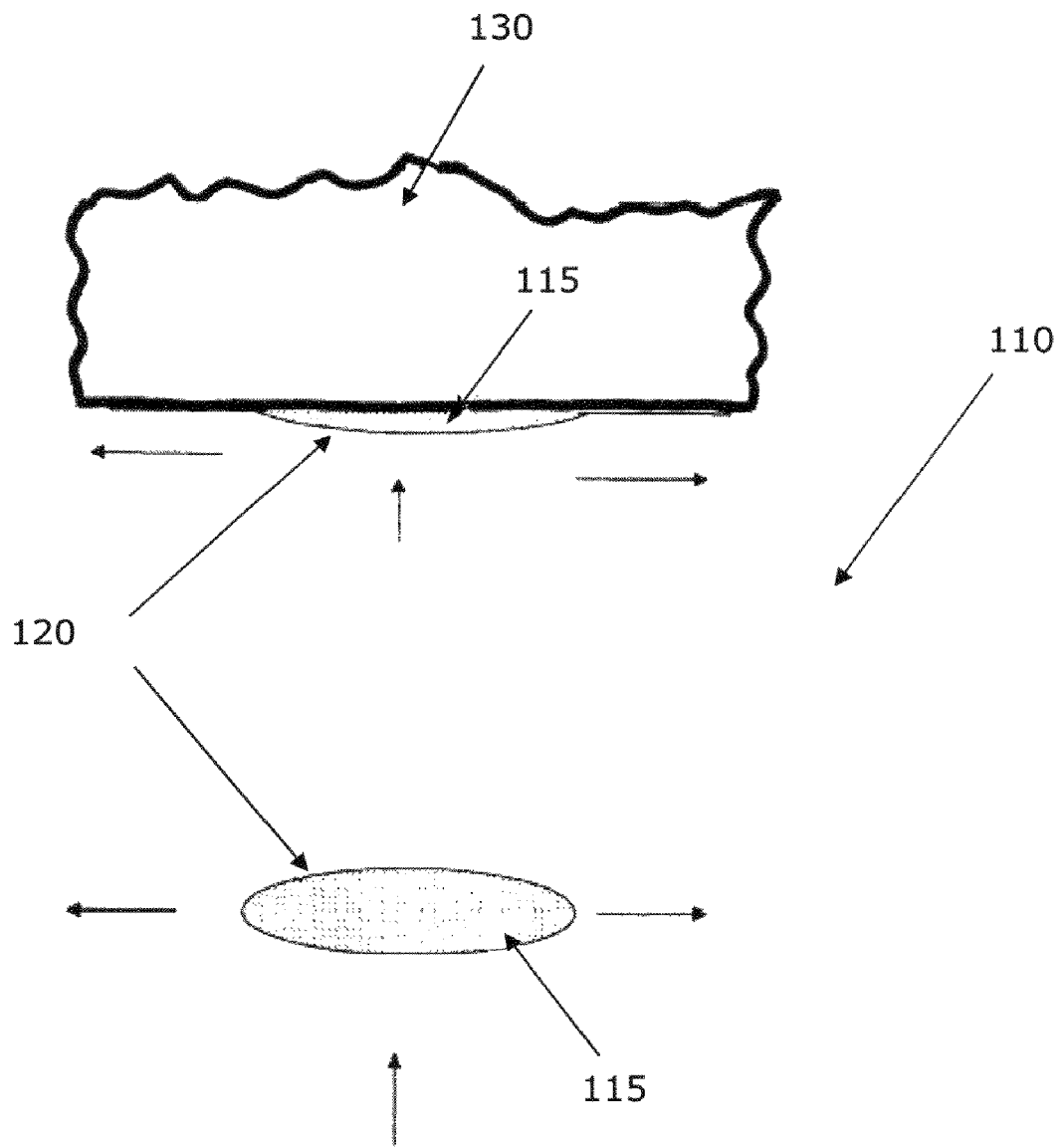

Furthermore, and looking now at FIG. 11, porous membrane 110 may be deployed in single or multiple layers substantially anywhere along shaft 105. In the case of a monorail balloon catheter or stent delivery system, the length of the porous membrane may be limited to the opening of the catheter shaft at the point at which the guidewire channel exits. A catheter of this construction may be used solely as a source of oxygen delivery or, alternatively, the catheter may be configured to deliver working tools, including visualization devices and atherectomy devices, to an internal site even as tissue downstream of the site has been, and continues to be, oxygenated by the gas-rich PFC.

In another preferred construction of the present invention, porous membrane 110 may be applied to the walls of balloon 140, in order to deliver oxygen (or another gas) directly to the walls of blood vessel 130. See, for example, FIGS. 12-16. In this construction, balloon 140 may donate oxygen and/or other gases to the bloodstream prior to balloon inflation, and thereafter topically apply the oxygen and/or other gases to the walls of the blood vessel during balloon inflation.

The present invention may be incorporated in still other embodiments.

Figure 17:
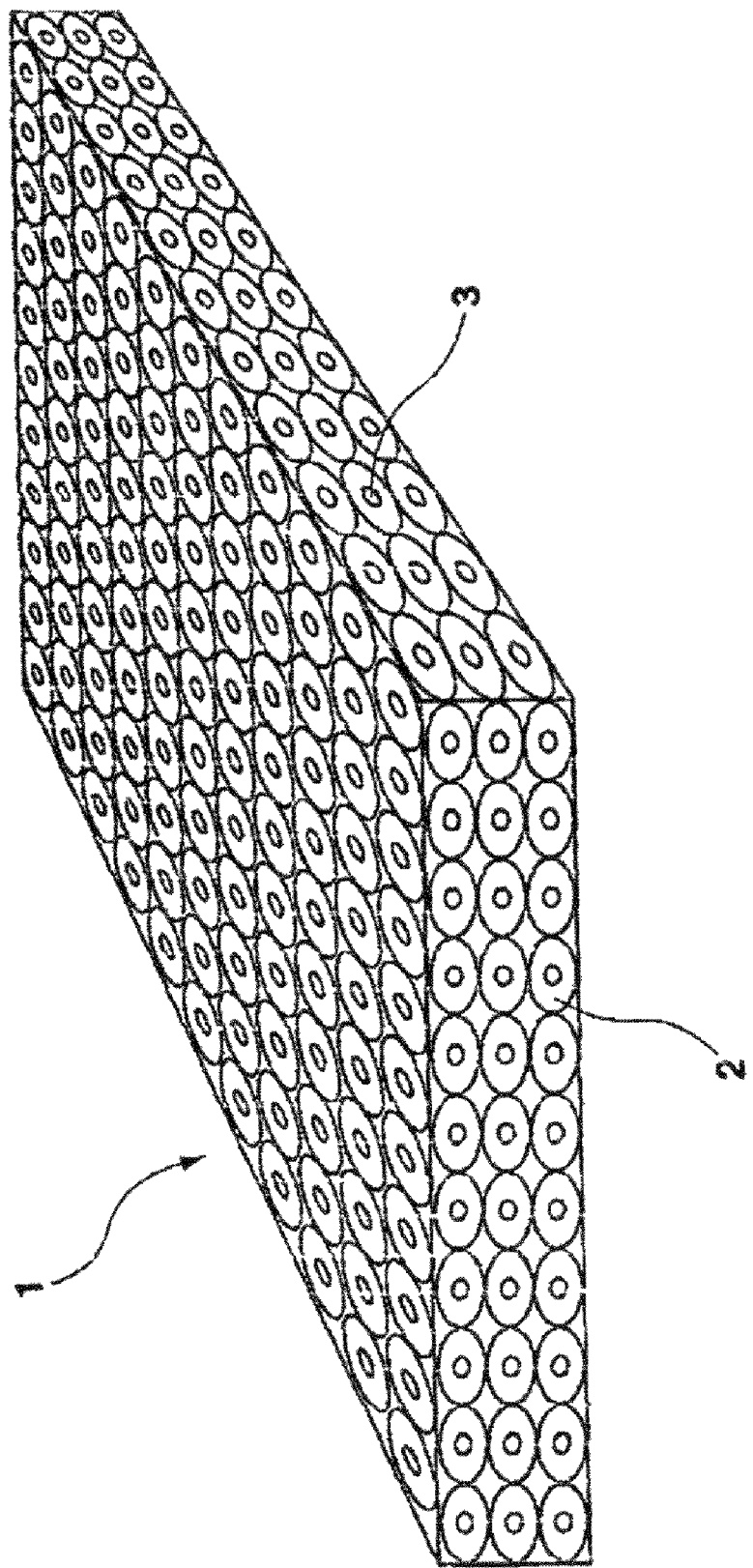
FIG. 17 is a schematic perspective view of a microporous, or nanoporous, thin film membrane, with the pores releasably storing the gas-rich (oxygen-rich) PFC in accordance with the present invention, wherein the microporous or nanoporous membrane may be (i) part of a medical device inserted into a blood vessel, and/or (ii) used as a tissue patch for the improved closure of wounds and/or the topical treatment of surface tissue.

Thus, for example, FIG. 17 shows a perspective view of a porous thin film membrane 1 with pores 2, functioning as a flexible porous substrate for a liquid oxygen carrier 3 in accordance with the present invention. An oxygenated perfluorocarbon (PFC) solution is incorporated in the porous substrate and elutes from the porous substrate. The liquid oxygen carrier (i.e., the oxygenated PFC) diffuses freely out of the porous thin film membrane. Studies on the release kinetics of the oxygenated perfluorocarbons (PFCs) from different polymer membranes show that dispersion of the oxygenated perfluorocarbon (PFC) solution from such a membrane into tissue or blood varies between minutes and several hours, depending on the temperature of the environment. Polymers with small pore sizes, preferably of 0.001-200 microns, produce an effective delivery mechanism for oxygenated perfluorocarbon (PFC) solutions. The temperature-dependent release feature of the porous membrane may be used for all of the vascular devices described herein such as tubes, balloons, endovascular stents, wires, atherectomy devices, or tissue patches aimed at modifying the oxygen supply to tissues of various body organs. The release kinetics from the substrate can be controlled by injection of fluids of 0-50° C. making direct or indirect contact with the porous substrate carrying the oxygenated perfluorocarbon (PFC) solution.

FIG. 18 shows a schematic longitudinal view of a balloon catheter 4, with the porous substrate 6 being tightly connected with the balloon 5, and with the porous substrate being impregnated with the oxygen carrier (i.e., the oxygen-rich PFC solution). The oxygen carrier solution is incorporated into a membrane 7 which is attached to the surface of the balloon. The liquid oxygen carrier is an oxygenated perfluorocarbon (PFC) solution. A "guidewire" lumen 8 allows positioning of the balloon in the artery with a wire. This guidewire may be a flexible wire 25 emitting ionizing radiation 26 from incorporated beta-particle emitters such as Sr-90/Y-90 (strontium/yttrium) or P-32 (phosphorus) or ultraviolet light (UV) waves 27. In the first case, the flexible wire 25 may be partially coated with the beta-particle-emitters 26 and in the latter case, the flexible wire 25 is an ultraviolet light waveguide connected to an ultraviolet light source and having a surface structure within the balloon 5 to radially emit the UV waves 27. The shaft of the catheter 9 includes an inflation channel 10 for inflation of a balloon with fluids or contrast agents to visualize the balloon under fluoroscopy.

FIG. 19 shows a schematic longitudinal view of a perfusion balloon catheter 11 serving as the substrate source 6 for the liquid oxygen carrier (i.e., the oxygenated PFC solution). In this embodiment, the oxygen delivery source membrane 7 is located on the surface of the balloon 5 and proximally 12 and distally 13 to the balloon end of the catheter 11 on the shaft 9 of the catheter. The shaft 9 of the perfusion balloon catheter includes the guidewire lumen 8, a balloon inflation lumen 14, and a perfusion fluid lumen 15. The perfusion fluid lumen 15 allows perfusion of blood or transport of therapeutic fluids (temperature between 0-50 degrees C.) through the inflated balloon. The perfusion fluid lumen 15 is designed to allow injection of therapeutic liquids or drugs with temperatures between 0 degrees C. and 50 degrees C. to modify the release kinetics of the oxygen carrier from the substrate. Holes beyond the proximal end 16 of the balloon connect a pathway for blood through the shaft 9 of the perfusion balloon catheter to the distal end of the catheter 17. The perfusion fluid lumen 15 connects to the holes at the proximal end 16 and distal end 17 of the balloon. The perfusion holes 16, 17 penetrate through the membrane 12, 13 carrying the liquid oxygen carrier (i.e., the PFC solution). Thus, blood perfusion through the balloon carries blood that is oxygenated by the membrane at the proximal end of the inflated balloon and is oxygenated beyond the distal end of the inflated balloon by the membrane after passage through the balloon. The guidewire 25 contains the oxygen carrier 7 at its distal tip 28. A stent 29 is mounted on the deflated balloon 5. Upon inflation of the balloon via its lumen 14, the stent 29 is expanded and deployed into the vessel.

Figure 20:
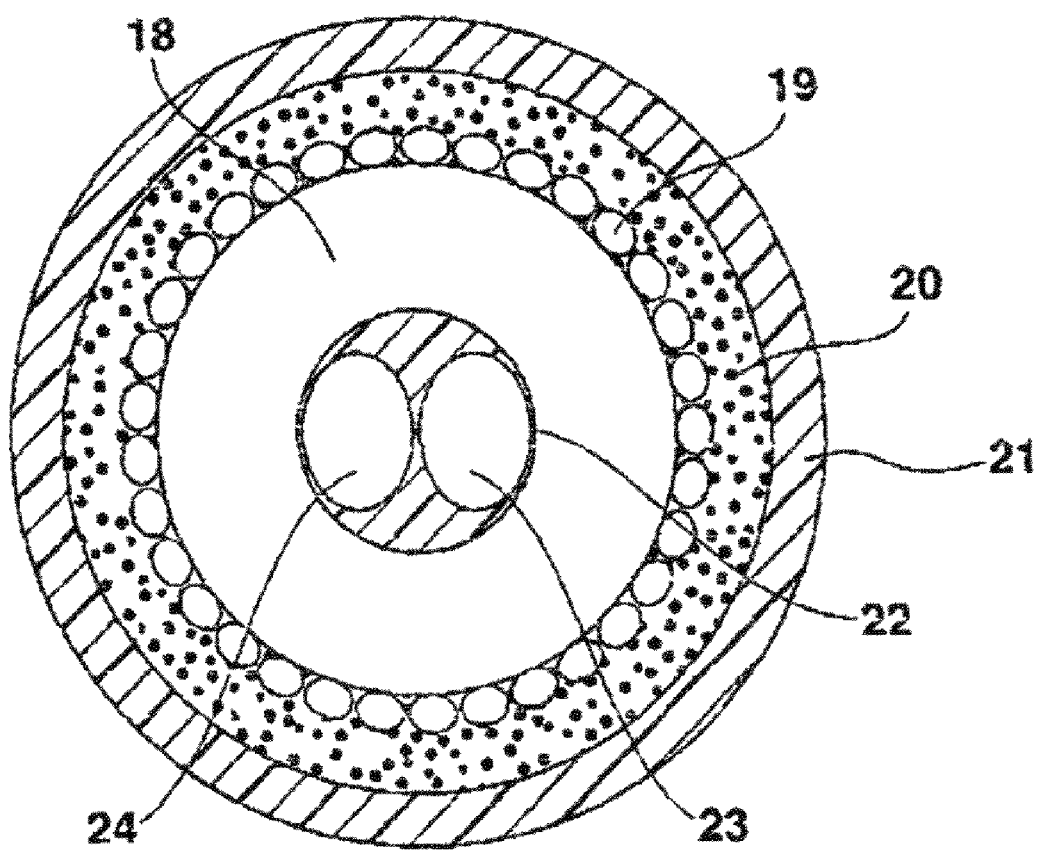
FIG. 20 is a schematic cross-sectional view of the distal part of a medical device (e.g., a catheter) containing a porous membrane holding a supply of gas-rich (e.g., oxygen-rich) PFC, with the porous membrane being encompassed by a housing which seals off the porous membrane (and its supply of gas-rich PFC) in accordance with the present invention.

FIG. 20 shows a schematic cross-sectional view of a medical device containing a liquid oxygen delivery source being encompassed by a removable housing sealing off the impregnated source in accordance with the present invention. The oxygen delivery source such as a perfusion balloon catheter 18 with an attached thin film membrane 19 incorporating the oxygen carrier (i.e., the oxygen-rich PFC solution) is placed in a container 21 filled with a liquid oxygen carrier solution 20. The container eliminates any dissipation of liquid or oxygen, and is used as a storage place for the oxygen delivery source. The inner part 22 of the shaft of the perfusion catheter contains a guidewire lumen 23 and perfusion fluid lumen 24 for the perfusion of blood or therapeutic fluids.

Figure 21:
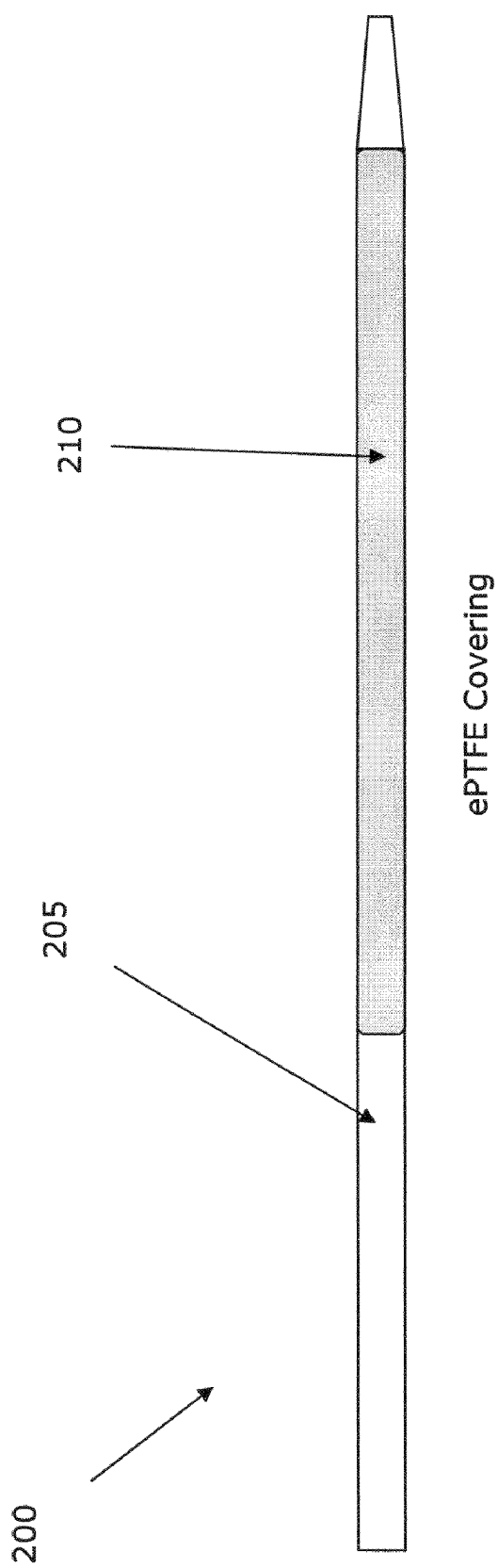
FIG. 21 is a schematic view showing a medical wire formed in accordance with the present invention, wherein the porous membrane is disposed on the exterior of the wire.

Looking next at FIG. 21, there is shown a medical wire 200. Medical wire 200 may be coronary wire, a guide wire, etc. Medical wire 200 comprises a shaft 205. At least a portion of shaft 205 comprises a porous membrane 210 for carrying a gas-rich (e.g., oxygen-rich) PFC solution in accordance with the present invention. Porous membrane 210 may be formed as an integral part of shaft 205, or it may be formed as a separate element and secured to shaft 205 in ways well known in the art (e.g., by bonding).

Figure 22:
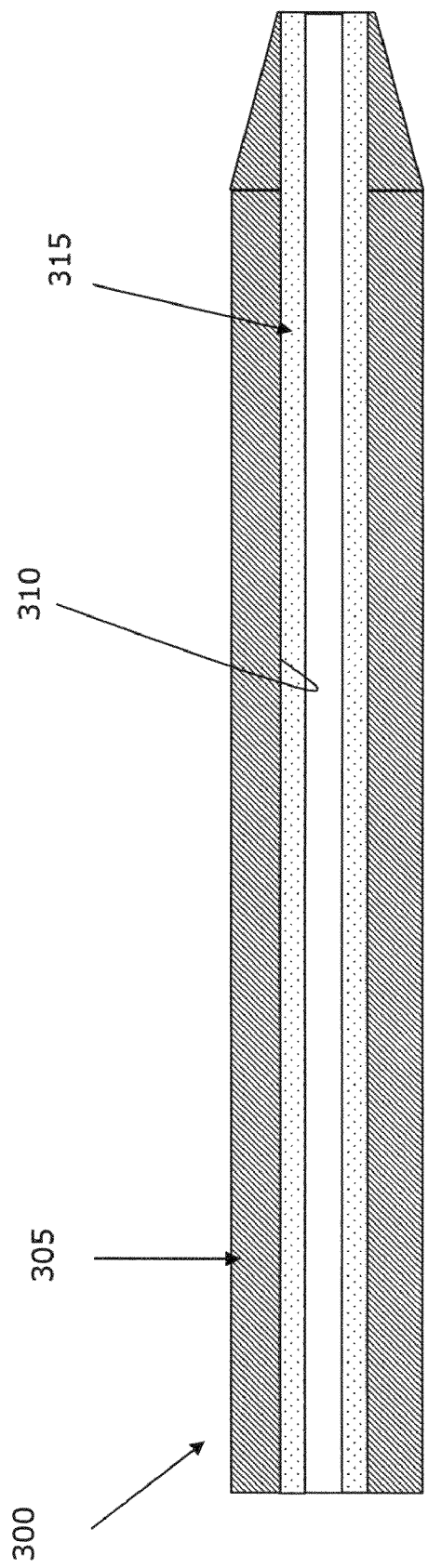
FIG. 22 is a schematic view showing a medical wire formed in accordance with the present invention, wherein the wire is cannulated, and further wherein the porous membrane is in the form of a tube disposed within the cannulated wire.

Looking next at FIG. 22, there is shown a medical wire 300. Medical wire 300 may be coronary wire, a guide wire, etc. Medical wire 300 comprises a shaft 305 and a central lumen 310. A porous membrane 315 is disposed within the interior of lumen 310. Porous membrane 315 is preferably in the form of a hollow tube disposed within lumen 310 of medical wire 300. Porous membrane 310 is constructed to carry a gas-rich (e.g., oxygen-rich) PFC solution in accordance with the present invention.

Figure 23:
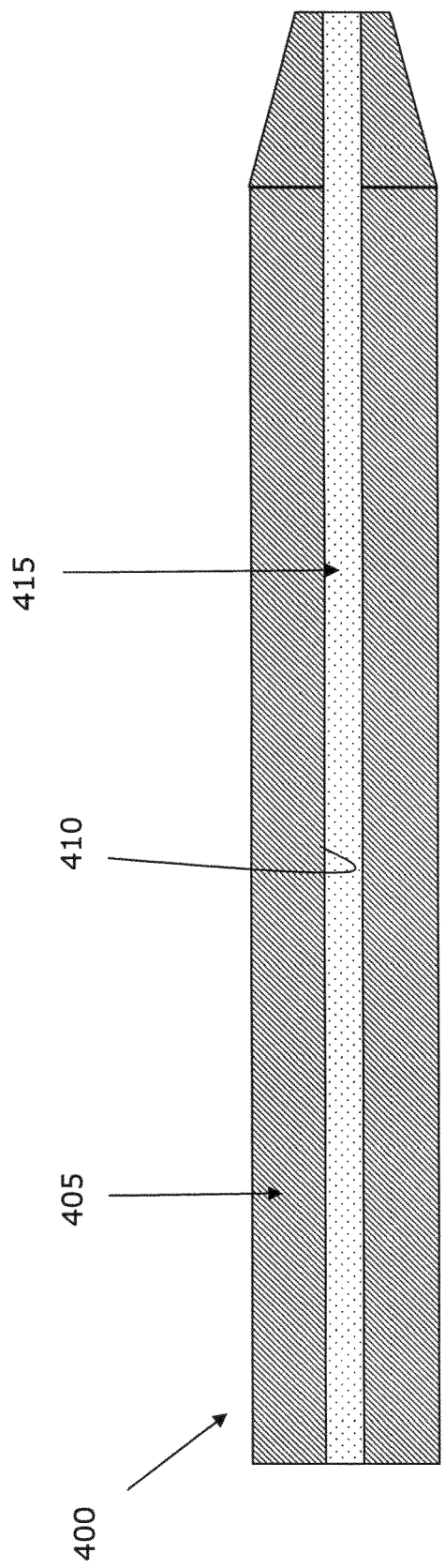
FIG. 23 is a schematic view showing a medical wire formed in accordance with the present invention, wherein the wire is cannulated, and further wherein the porous membrane is in the form of a wick disposed within the interior of the cannulated wire.

Looking next at FIG. 23, there is shown a medical wire 400. Medical wire 400 may be a coronary wire, a guidewire, etc. Medical wire 400 comprises a shaft 405 and a central lumen 410. A porous membrane 415 is disposed within the interior of lumen 410. Porous membrane 415 is preferably in the form of a single body substantially completely filling lumen 410 so as to form a wick-like structure. Porous membrane 415 is constructed so as to carry a gas-rich (e.g., oxygen-rich) PFC solution, and safely dispense the same into the bloodstream without the creation of dangerous embolisms, in accordance with the present invention. Furthermore, because porous membrane 415 is configured to form a wick-like structure within shaft 405 of medical wire 400, porous membrane 415 can be used to transport gas-rich (e.g., oxygen-rich) PFC to the distal tip of medical wire 400, whereupon the gas-rich PFC may be safely released into the bloodstream.

In one preferred construction, and as shown in FIG. 23, porous membrane 415 extends all of the way from the proximal end of medical wire 400 to the distal tip of medical wire 400. In this construction, porous membrane 415 can be pre-loaded with the gas-rich PFC solution prior to deploying the medical wire in the bloodstream of the patient. Alternatively, with this construction, the proximal end of porous membrane 415 can be placed in contact with a reservoir of gas-rich PFC after medical wire 400 has been deployed in the bloodstream of the patient, whereupon porous membrane 415 will "wick" the gas-rich PFC solution from the proximal end of porous membrane 415 to the distal tip of porous membrane 415, where it is released into the bloodstream of the patient.

In another preferred construction, porous membrane 415 extends along only a portion of lumen 410. More particularly, in this alternative construction, porous membrane 415 extends from the distal tip of medical wire 400 back along a portion of the length of lumen 410. In this construction, the gas-rich PFC solution can be introduced into the proximal end of lumen 410 (either before or after medical wire 400 is deployed in the patient), whereupon porous membrane 415 will "wick" the gas-rich PFC solution down the remainder of lumen 410 to the distal tip of porous membrane 415, where it is released into the bloodstream of the patient.

The invention described herein consists of a gas (e.g., $O_2$, NO, CO, etc., or a combination of these gases) delivery source for local rescue of ischemic tissue. The invention consists of porous polymer membranes being part of a medical device from which a liquid gas carrier (i.e., the gas-rich PFC) is locally or systemically released. The porous membrane impregnated with the liquid gas carrier may be a part of a tube, a balloon, a perfusion balloon, a stent, and a wire. The porous membrane is preferably sealed with a removable housing to allow storage of the medical device.

MODIFICATIONS

It is to be understood that the present invention is by no means limited to the particular constructions herein disclosed and/or shown in the drawings, but also comprises any modifications or equivalents within the scope of the invention.

What is claimed is:

1. A system comprising:
   a hollow tube having a distal end, a proximal end, and a lumen extending between the distal end and the proximal end;
   at least a portion of the tube comprising a porous membrane; and
   a gas-rich perfluorocarbon solution incorporated in the porous membrane;
   wherein the porous membrane has a porosity in the range of 0.001-200 microns, in order that:
   (i) the gas-rich perfluorocarbon solution is effectively incorporated into the porous membrane; and
   (ii) when the porous membrane is positioned in blood, the gas-rich perfluorocarbon solution elutes out of the porous membrane, in aggregations small enough to prevent the creation of embolisms in the blood, with the elution of the gas-rich perfluorocarbon solution into the blood varying between minutes and several hours, depending on the temperature and the hemodynamics of the blood.

2. A system according to claim 1 wherein at least a portion of the porous membrane is located within the hollow tube.

3. A system according to claim 2 wherein the porous membrane substantially fills the lumen along substantially the entire length of the lumen.

4. A system according to claim 3 wherein the porous membrane substantially fills the lumen along only a portion of the length of the lumen.

5. A system according to claim 4 wherein the porous membrane fills the distal end of the lumen.

6. A system according to claim 1 wherein at least a portion of the porous membrane is located on an outer surface of the hollow tube.

7. A system according to claim 1 wherein the hollow tube and the porous membrane are configured so that liquid may pass through the porous membrane as it enters and exits the lumen.

8. A system according to claim 1 wherein the hollow tube comprises an inflatable balloon.

9. A system according to claim 8 wherein the porous membrane is mounted to a surface of the balloon.

10. A system according to claim 8 wherein the hollow tube and inflatable balloon are in the form of a balloon catheter.

11. A system according to claim 1 further comprising a removable housing disposed around the porous membrane.

12. A system according to claim 1 wherein the hollow tube further comprises a plurality of holes formed in the sidewall of the hollow tube and communicating with the lumen of the hollow tube, and further wherein the porous membrane is disposed adjacent to the plurality of holes.

13. A system according to claim 1 wherein the system further comprises a coronary wire.

14. A system according to claim 13 wherein a tip of the coronary wire comprises a porous membrane,
wherein a gas-rich perfluorocarbon solution is incorporated in the porous membrane, and further wherein the porous membrane has a porosity in the range of 0.001-200 microns, in order that:
(i) the gas-rich perfluorocarbon solution is effectively incorporated into the porous membrane; and
(ii) when the porous membrane is positioned in blood, the gas-rich perfluorocarbon solution elutes out of the porous membrane, in aggregations small enough to prevent the creation of embolisms in the blood, with the elution of the gas-rich fluorocarbon solution into the blood varying between minutes and several hours, depending on the temperature and the hemodynamics of the blood.

15. A system according to claim 13 wherein the coronary wire further comprises an ionizing radiation source.

16. A system according to claim 15 wherein the ionizing radiation source comprises a beta-particle emitter.

17. A system according to claim 13 wherein the coronary wire further comprises an ultraviolet light source.

18. A system according to claim 1 wherein the porous membrane comprises a porous polymer.

19. A system according to claim 18 wherein the porous polymer is selected from the group consisting of polytetrafluoroethylene, polyethylene, polyethylene terephtalate, nylon, silicone, and cellulose acetate.

20. A system according to claim 1 wherein the porous membrane is lipophilic.

21. A system according to claim 1 wherein the system further comprises a housing for protectively covering the porous membrane in order to prevent the loss of the gas-rich perfluorocarbon solution and/or gas.

22. A system according to claim 1 wherein the system further comprises a fluid for passage through the lumen, and further wherein the fluid is at a temperature of between about 0° C. and about 50° C.

23. A system according to claim 1 wherein the hollow tube further comprises a stent.

24. A system according to claim 1 wherein the lumen of the hollow tube is configured to modulate release kinetics of the gas-rich perfluorocarbon solution by enabling fluid injection at temperatures between about 0° C. and about 50° C.

25. A system according to claim 1 wherein the gas-rich perfluorocarbon solution comprises an oxygen-rich perfluorocarbon solution, and further wherein the porous membrane has a porosity in the range of 20-200 microns.

26. A system according to claim 1 wherein the porous membrane comprises a plurality of layers, with the plurality of layers being deployed one on top of another.

27. A system according to claim 26 wherein the porosity of a least two of the layers vary from one another.

28. A system according to claim 27 wherein an inner-more layer has a larger porosity than an outer-more layer.

29. A system according to claim 27 wherein the gas-rich perfluorocarbon solution comprises an oxygen-rich perfluorocarbon solution, and further wherein the outermost layer has a porosity in the range of 20-200 microns, and an inner-more layer has a porosity greater than 200 microns.

30. A system according to claim 1 wherein the hollow tube comprises a catheter.

31. A system according to claim 1 wherein the hollow tube comprises a medical wire.

32. A system comprising:
a medical wire;
at least a portion of the medical wire comprising a porous membrane; and
a gas-rich perfluorocarbon solution incorporated in the porous membrane;
wherein the porous membrane has a porosity in the range of 0.001-200 microns, in order that:
(i) the gas-rich perfluorocarbon solution is effectively incorporated into the porous membrane; and
(ii) when the porous membrane is positioned in blood, the gas-rich perfluorocarbon solution elutes out of the porous membrane, in aggregations small enough to prevent the creation of embolisms in the blood, with the elution of the gas-rich fluorocarbon solution into the blood varying between minutes and several hours, depending on the temperature and the hemodynamics of the blood.

33. A system according to claim 32 wherein the porous membrane comprises a porous polymer.

34. A system according to claim 33 wherein the porous polymer is selected from the group consisting of polytetrafluoroethylene, polyethylene, polyethylene terephtalate, nylon, silicone, and cellulose acetate.

35. A system according to claim 32 wherein the porous membrane is lipophilic.

36. A system according to claim 32 wherein the system further comprises a housing for protectively covering the porous membrane in order to prevent the loss of the gas-rich perfluorocarbon solution and/or gas.

37. A system according to claim 32 wherein the gas-rich perfluorocarbon solution comprises an oxygen-rich perfluorocarbon solution, and further wherein the porous membrane has a porosity in the range of 20-200 microns.

38. A system according to claim 32 wherein the porous membrane comprises a plurality of layers, with the plurality of layers being deployed one on top of another.

39. A system according to claim 38 wherein the porosity of a least two of the layers vary from one another.

40. A system according to claim 39 wherein an inner-more layer has a larger porosity than an outer-more layer.

41. A system according to claim 40 wherein the gas-rich perfluorocarbon solution comprises an oxygen-rich perfluorocarbon solution, and further wherein the outermost layer has a porosity in the range of 20-200 microns, and an inner-more layer has a porosity greater than 200 microns.

42. A system according to claim 32 wherein the medical wire comprises a coronary wire.

43. A system according to claim 32 wherein the medical wire comprises a guidewire.

44. A method for treating a patient, comprising:
providing:
(i) a hollow tube having a distal end, a proximal end, and a lumen extending between the distal end and the proximal end, at least a portion of the tube comprising a porous membrane; and
(ii) a gas-rich perfluorocarbon solution;
loading the gas-rich perfluorocarbon solution into the porous membrane; and
positioning the tube in the vascular system of the patient so that porous membrane is exposed to blood;
wherein the porous membrane has a porosity in the range of 0.001-200 microns, in order that:
(i) the gas-rich perfluorocarbon solution is effectively incorporated into the porous membrane; and
(ii) when the porous membrane is positioned in blood, the gas-rich perfluorocarbon solution elutes out of the porous membrane, in aggregations small enough to prevent the creation of embolisms in the blood, with the elution of the gas-rich perfluorocarbon solution into the blood varying between minutes and several hours, depending on the temperature and the hemodynamics of the blood.

45. A method according to claim 44 wherein the gas-rich perfluorocarbon solution comprises an oxygen-rich perfluorocarbon solution, and further wherein the porous membrane has a porosity in the range of 20-200 microns.

46. A method according to claim 44 wherein loading the gas-rich perfluorocarbon solution into the porous membrane comprises immersing the porous membrane in a vial containing the gas-rich perfluorocarbon solution.

47. A method for treating a patient, comprising:
providing:
(i) a medical wire, at least a portion of the medical wire comprising a porous membrane; and
(ii) a gas-rich perfluorocarbon solution;
loading the gas-rich perfluorocarbon solution into the porous membrane; and
positioning the medical wire in the vascular system of the patient so that porous membrane is exposed to blood;
wherein the porous membrane has a porosity in the range of 0.001-200 microns, in order that:
(i) the gas-rich perfluorocarbon solution is effectively incorporated into the porous membrane; and
(ii) when the porous membrane is positioned in blood, the gas-rich perfluorocarbon solution elutes out of the porous membrane, in aggregations small enough to prevent the creation of embolisms in the blood, with the elution of the gas-rich perfluorocarbon solution into the blood varying between minutes and several hours, depending on the temperature and the hemodynamics of the blood.

48. A method according to claim 47 wherein the gas-rich perfluorocarbon solution comprises an oxygen-rich perfluorocarbon solution, and further wherein the porous membrane has a porosity in the range of 20-200 microns.

49. A method according to claim 48 wherein loading the gas-rich perfluorocarbon solution into the porous membrane comprises immersing the porous membrane in a vial containing the gas-rich perfluorocarbon solution.

50. An intravascular treatment device comprising:
an intravascular device having a distal end and a proximal end;
at least a portion of the intravascular device comprising a porous membrane; and
a perfluorocarbon solution incorporated in the porous membrane;
wherein the porous membrane has a porosity in the range of 0.001-200 microns, in order that:
(i) the perfluorocarbon solution is effectively incorporated into the porous membrane; and
(ii) when the porous membrane is positioned in blood, the perfluorocarbon solution elutes out of the porous membrane, in aggregations small enough to prevent the creation of embolisms in the blood.

51. An intravascular treatment device according to claim 50 wherein the intravascular device comprises a hollow tube having a lumen formed therein.

52. An intravascular treatment device according to claim 50 wherein the intravascular device comprises a medical wire.

53. An intravascular treatment device according to claim 50 wherein the perfluorocarbon solution carries a therapeutic gas therein.

54. An intravascular treatment device according to claim 53 wherein the therapeutic gas comprises at least one of the group consisting of oxygen, nitric oxide and carbon monoxide.

55. An intravascular treatment device according to claim 50 wherein the perfluorocarbon solution does not carry a therapeutic gas therein.

56. A method for treating a patient, comprising:
providing:
an intravascular device having a distal end and a proximal end;
at least a portion of the intravascular device comprising a porous membrane; and
a perfluorocarbon solution;
loading the perfluorocarbon solution into the porous membrane; and
positioning the intravascular device in the vascular system of the patient so that porous membrane is exposed to blood;
wherein the porous membrane has a porosity in the range of 0.001-200 microns, in order that:
(i) the perfluorocarbon solution is effectively incorporated into the porous membrane; and
(ii) when the porous membrane is positioned in blood, the perfluorocarbon solution elutes out of the porous membrane, in aggregations small enough to prevent the creation of embolisms in the blood.

* * * * *